(12) United States Patent
Onuchic et al.

(10) Patent No.: US 12,367,978 B2
(45) Date of Patent: Jul. 22, 2025

(54) METHODS AND SYSTEMS FOR DETERMINING SOMATIC MUTATION CLONALITY

(71) Applicant: Illumina, Inc., San Diego, CA (US)

(72) Inventors: Vitor Ferreira Onuchic, San Diego, CA (US); Kristina M. Kruglyak, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1208 days.

(21) Appl. No.: 16/208,290

(22) Filed: Dec. 3, 2018

(65) Prior Publication Data
US 2019/0172582 A1 Jun. 6, 2019

Related U.S. Application Data

(60) Provisional application No. 62/593,810, filed on Dec. 1, 2017.

(51) Int. Cl.
| | | |
|---|---|---|
| G16H 50/20 | (2018.01) |
| C12Q 1/6806 | (2018.01) |
| C12Q 1/6809 | (2018.01) |
| C12Q 1/6827 | (2018.01) |
| C12Q 1/6886 | (2018.01) |
| G06F 17/15 | (2006.01) |
| G16B 20/10 | (2019.01) |
| G16B 20/20 | (2019.01) |
| G16B 40/00 | (2019.01) |
| G16H 50/30 | (2018.01) |

(52) U.S. Cl.
CPC .......... *G16H 50/20* (2018.01); *C12Q 1/6806* (2013.01); *C12Q 1/6809* (2013.01); *C12Q 1/6827* (2013.01); *C12Q 1/6886* (2013.01); *G06F 17/153* (2013.01); *G16B 20/10* (2019.02); *G16B 20/20* (2019.02); *G16B 40/00* (2019.02); *G16H 50/30* (2018.01)

(58) Field of Classification Search
CPC ........ G16H 50/20; G16H 50/30; G16B 20/20; G16B 40/00; G16B 20/10; C12Q 1/6806; C12Q 1/6809; C12Q 1/6827; C12Q 1/6886; G06F 17/153
See application file for complete search history.

(56) References Cited

U.S. PATENT DOCUMENTS

| | | |
|---|---|---|
| 7,601,499 B2 | 12/2009 | Berka |
| 2009/0026082 A1 | 1/2009 | Rothberg et al. |
| 2012/0053063 A1 | 3/2012 | Rigatti et al. |
| 2013/0029852 A1 | 1/2013 | Rava et al. |
| 2015/0197785 A1 | 7/2015 | Carter et al. |
| 2016/0210402 A1 | 7/2016 | Zamani Esteki et al. |
| 2016/0333416 A1 | 11/2016 | Babiarz et al. |

FOREIGN PATENT DOCUMENTS

| | | |
|---|---|---|
| CA | 2945962 A1 | 10/2015 |
| CN | 101155932 A | 4/2008 |
| CN | 101437962 A | 5/2009 |
| CN | 103562218 A | 2/2014 |
| CN | 104781421 A | 7/2015 |
| CN | 105408496 A | 3/2016 |
| CN | 106164289 A | 11/2016 |
| CN | 106460070 A | 2/2017 |
| CN | 107075482 A | 8/2017 |
| CN | 107075586 A | 8/2017 |
| CN | 107206064 A | 9/2017 |
| CN | 107406876 A | 11/2017 |
| WO | WO-2014026096 A1 | 2/2014 |
| WO | WO-2015164432 A1 | 10/2015 |
| WO | WO-2016127944 A1 | 8/2016 |
| WO | WO-2017042394 A1 | 3/2017 |
| WO | WO-2019109086 A1 | 6/2019 |

OTHER PUBLICATIONS

Gubin et al. "Tumor neoantigens: building a framework for personalized cancer immunotherapy." The Journal of Clinical Investigation, vol. 125(9): pp. 3413-3421. (Year: 2015).*
Richards, O. , et al., "Chemical mechanism of sonic, acid, alkaline and enzymic degradation of DNA", J Mol Biol 11, Feb. 1965, 327-340.
Andrew Roth et al: "PyClone: statistical inference of clonal population structure in cancer", Nature Methods, vol. 11, No. 4, Mar. 16, 2014 (Mar. 16, 2014), pp. 396-398, XP055563468, New York ISSN: 1548-7091, DOI: 10.1038/nmeth.2883.
International Preliminary Report on Patentability dated Jun. 11, 2020 issued in PCT Application No. PCT/US2018/063647.
International Search Report and Written Opinion dated Mar. 18, 2019 issued in PCT Application No. PCT/US2018/063647.
Niccolo Bolli et al: "Heterogeneity of genomic evolution and mutational profiles in multiple myeloma", Nature Communications, vol. 5, No. 1, Dec. 1, 2014 (Dec. 1, 2014), pp. 2997-2997, XP055563476, GB ISSN: 2041-1723, DOI: 10.1038/ncomms3997.
"Human Genome Browser—hg18 assembly", http://genome.ucsc.edu/cgi-bin/hgGateway?org=Human&db=hg18&hgsid=166260105.
"Human Genome Browser—hg19 assembly", https://genome.ucsc.edu/cgi-bin/hgGateway?db=hg19.

(Continued)

Primary Examiner — Kaitlyn L Minchella
Assistant Examiner — Steven W. Bailey
(74) Attorney, Agent, or Firm — Weaver Austin Villeneuve & Sampson LLP

(57) ABSTRACT

Computer implemented methods and computer systems are provided for estimating cancer cell fractions indicating proportions of cancer cells carrying one or more mutations of interest using one or more nucleic acid samples from a subject. The methods and systems provided herein implement processes that use a variational Bayesian mixture model to cluster initial cancer cell fractions and obtain the one or more final cancer cell fractions, the initial cancer cell fractions accounting for cancer purity and copy numbers. The disclosed methods and systems improve accuracy, validity, and reliability of tests for cancer clonality, and save time, materials, cost, and computer resources required for the tests, which can help design more affective cancer treatments.

37 Claims, 25 Drawing Sheets

(56) References Cited

OTHER PUBLICATIONS

Alnemri, E., et al., "Activation of internucleosomal DNA cleavage in human CEM lymphocytes by glucocorticoid and hovobiocin. Evidence for a non-Ca2(+)-requiring mechanism(s).", J Biol. Chem 265(28), 1990, 17323-17333.
Altschul, et al., "Basic Local Alignment Search Tool", J. Mol. Biol. 1990. pp. 403-410, vol. 215., 1990, 403-410.
Bentley, et al., "Accurate whole human genome sequencing using reversible terminator chemistry", Nature, vol. 456, 2008, 53-59.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Chen, et al., "Microsatellite alterations in plasma DNA of small cell lung cancer patients", Nat Med. 2(9), 1996, 1033-5.
Ding, L., et al., "Clonal evolution in relapsed acute myeloid leukemia revealed by whole genome sequencing", Nature 481(7382), Jul. 26, 2012, 506-510.
Fan, et al., "Noninvasive diagnosis of fetal aneuploidy by shotgun sequencing DNA from maternal blood", Proceedings of the National Academy of Sciences, Oct. 21, 2008, 16266-71.
Harris, et al., "Single-Molecule DNA Sequencing of a Viral Genome", Science 320, Apr. 4, 2008, 106-109 and Suppl. Materials 1-25.
Koide, et al., "Fragmentation of cell-free fetal DNA in plasma and urine of pregnant women", Prenat Diagn. Jul. 2005;25(7), www.interscience.wiley.com, Mar. 14, 2005, 604-7.
Kozarewa, et al., "Amplification-free Illumina sequencing-library preparation facilitates improved mapping and assembly of GC-biased genomes", Nat. Methods, 6(4), Apr. 2009, 291-295.
Langmead, et al., "Ultrafast and memory-efficient alignment of short DNA sequences to the human genome", Genome Biology, vol. 10, 2009, R25.1-R25.10.
Lo, et al., "Presence of fetal DNA in maternal plasma and serum", Lancet. 350(9076), Aug. 16, 1997, 485-487.
Ma, Q., et al., "Opening Pandora's Box—the new biology of driver mutations", Curr Opin Genet Dev 22(1), Feb. 2012, 3-9.
Margulies, et al., "Genome sequencing in microfabricated high-density picolitre reactors", Nature, vol. 437, 2005, 376-380 and Supplemental Materials.
McGranahan, N., et al., "Clonal neoantigens elicit T cell immunoreactivity and sensitivity to immune checkpoint plockade.", Science 352(6280), Mar. 3, 2016, 1463-9.
Merlo, L., et al., "A Comprehensive Survey of Clonal Diversity Measures in Barrett's Esophagus as Biomarkers of Progression to Esophageal Adenocarcinoma", Cancer Prev Res 3(11), Oct. 12, 2010, 1388-1397.
Rizvi, N., et al., "Mutational landscape determines sensitivity to PD-1 blockade in non-small cell lung cancer", Science 348(6230), Apr. 3, 2015, 124-128.
Roth, A., et al., "PyClone: Statistical inference of clonal population structure in cancer", Nat Methods, Mar. 16, 2014, 396-398.
Soni, et al., "Progress toward Ultrafast DNA Sequencing Using Solid-State Nanopores", Clin Chem, 53(11), 2007, 1996-2001.
Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.
Yap, T., et al., "Intratumor Heterogeneity: Seeing the Wood for the Trees", Science Translational Medicine 4(127), Mar. 28, 2012, 1-5.
Roller et al., "Canvas: versatile and scalable detection of copy number Variants," Bioinformatics, vol. 32, Issue 15, Aug. 1, 2016, pp. 2375-2377, https://doi.org/10.1093/bioinformatics/btw163 Published: Mar. 24, 2016, 10 pages.
Guilhoto, "Applying Markov Chains to Monte Carlo Integration," http://math.uchicago.edu/~may/REU2017/REUPapers/Guilhoto.pdf, 2017, 16 pages.
Miller et al., "SciClone: Inferring Clonal Architecture and Tracking the Spatial and Temporal Patterns of Tumor Evolution," PLOS Computational Biology | www.ploscompbiol.org, vol. 10, Issue 8, e1003665, Aug. 2014, 15 pages.
Bolli, N., et al., "Heterogeneity of genomic evolution and mutational profiles in mutiple myeloma", Nature Communications 5 (2997), Jan. 16, 2014, 1-13.
PCT/US2018/063647, "International Search Report and Written Opinon", Mar. 18, 2019, 1-17.
EP Office Action dated Aug. 5, 2022 in Application No. EP18821927.3.
JP Office Action dated Dec. 12, 2022 in Application No. JP2019-569695 with English translation.
Landau, D.A. et al., "Evolution and Impact of Subclonal Mutations in Chronic Lymphocytic Leukemia", Cell, Feb. 14, 2013, vol. 152, No. 4, pp. 714-726.
Australian Examination Report dated Aug. 15, 2023, in Application No. AU2018375008.
CN Office Action dated Jan. 20, 2023 in Application No. CN201880040456.7.
CN Office Action dated Aug. 5, 2023 in CN application No. 201880040456.7 with English Translation.
Dentro, S C., et al., "Principles of Reconstructing the Subclonal Architecture of Cancers," Cold Spring Harbor Perspectives in Medicine, 2017, vol. 7 (8), pp. 1-16.

\* cited by examiner

METHODS AND SYSTEMS FOR DETERMINING SOMATIC MUTATION CLONALITY

CROSS REFERENCE TO RELATED APPLICATIONS

This application claims benefits under 35 U.S.C. § 119(e) to U.S. Provisional Patent Application No. 62/593,810, entitled: CLONSCORE: FAST AND ACCURATE INFERENCE OF CLONALITY OF SOMATIC MUTATIONS, filed Dec. 1, 2017, which is herein incorporated by reference in its entirety for all purposes.

BACKGROUND

Cancers involve abnormal cell growth with the potential to invade or spread to other parts of the body. Cancers are largely driven by somatic mutations. Cancer cells through mutation gain the ability grow in an unchecked manner to usurp the organism. Many of the somatic mutations are clonal mutations and occur in a founding cell to initiate disease. These clonal mutations become uniformly present in the tumor by passing mutations to the cell's progeny during clonal expansion. The population of cells that are clones of the founding cell is also referred to as a clone in this disclosure. Other somatic mutations are sub-clonal, which occur in an existing neoplastic cell and are passed on only to the subpopulation of cells derived from it. The subpopulation of cells is also referred to as a subclone herein. The cells in a subclone have the founding mutations and the subclonal mutations. The result of the accumulation of clonal and sub-clonal mutations is a tumor that is composed of a heterogeneous mixture of cells. An emerging picture from recent studies across various solid and hematological cancers is that cancers are both spatially and temporally heterogeneous and are frequently comprises of a single founding clone and several subclones.

Intra-tumor heterogeneity and clonal architecture have clinical implications and contribute to therapy resistance. Ma et al., (2012), Curr Opin Genet Dev 22: 3-9. Yap T A, Gerlinger M, Futreal P A, Pusztai L, Swanton C (2012), Sci Transl Med 4: 127ps10. The presence of subclones has been linked to poor clinical outcome in chronic lymphocytic leukemia, or to increased risk of progression to malignancy, such as in Brett's esophagus and multiple myeloma. Subclonal mutations can drive resistance, as shown in EGF are muted non-small cell lung cancers. Merlo L M, Shah N A, Li X, Blount P L, Vaughan T L, et al. (2010), Cancer Prev Res (Phila) 3: 1388-97.

Developing effective cancer therapies requires an understanding of both the mutations underlying the cancer and its clonal structure. A number of characteristics of the clonal structure of tumors are of clinical significance in this context. For example, the number of subclones in the cancer cells may relate to drug resistance or is malignancy. Moreover, cancer cell fraction (CCF) measuring the fraction of cancer cells that carries a mutation of interest may affect the efficacy of a therapy targeting the mutation or its correlates. For example, somatic mutations can lead to creation of new antigens. Neoantigens are antigens generated by protein changing DNA mutations in tumor cells. Neoantigen can potentially be recognized by the immune system as non-self. Neoantigen load is a marker of response to immune checkpoint inhibitors. It has been shown that neoantigens level positively correlates with efficacy of anti-PD-1 therapy comprising administering pembrolizumab in non-small cell lung cancer. Rizvi et al. (2015), Science, 348 (6230): 124-128. The CCF of a mutation targeted by an immunotherapy therefore can affect therapy efficacy.

Therefore, methods and systems for measuring cancer clonal structure and properties have important implications for developing effective cancer treatments.

SUMMARY

Some implementations presented herein provide computer-implemented methods and systems for estimating CCF for one or more variants in one or more samples from a subject. In some implementations, the nucleic acid cancer samples include biological tissues, cells, peripheral blood, saliva, urine, and other biological fluid, as described below.

Because various methods and systems provided herein implement strategies and processes that use variational Bayesian mixture models to estimate CCF taking into considerations of copy number variations (CNVs) that may overlap with simple nucleotide variants (SNVs), these embodiments provide various technological improvements over conventional methods in estimating CCF for cancer samples. Some implementations provide improved analytical sensitivity and specificity, achieving more accurate estimates and faster results while using less computer memory and resources.

An aspect of the disclosure provides a computer implemented method for estimating CCF in one or more cancer samples of a subject. The method involves: (a) receiving, by the one or more processors, genomic sequence data obtained by sequencing nucleic acids in at least one test sample from a subject, wherein the nucleic acids are from one or more subclones of cancer cells; (b) determining a plurality of somatic mutation variants in the genomic sequence data; (c) calculating, for each somatic mutation variant and by the one or more processors, an initial cancer cell fraction (iCCF) using a VAF, wherein a cancer cell fraction is a fraction of cancer cells having the somatic mutation variant among all cancer cells, and wherein the VAF is an allele frequency of the somatic mutation variant, thereby obtaining a plurality of iCCFs for the plurality of somatic mutation variants; (d) clustering, by the one or more processors, the plurality of iCCFs for the plurality of loci, thereby obtaining one or more clusters of iCCFs, each cluster corresponding to variants present in a same subclone of the one or more tumor subclones; and (e) determining, by the one or more processors, one or more final cancer cell fractions (fCCFs) for one or more somatic mutations of the plurality of somatic mutations using iCCFs of the one or more clusters.

In some implementations, the method further includes: aligning sequence reads of the genomic sequence data to a reference genome to provide sequence tags, wherein the reference genome includes a plurality of loci, each locus of the plurality of loci harboring a somatic mutation of a plurality of somatic mutations; and determining, for each locus of the plurality of loci, a coverage of the locus and a variant allele frequency (VAF) of the locus.

In some implementations, the method further includes estimating a tumor purity value (p) that is a fraction of tumor cells among all cells in the test sample using the genomic sequence data.

In some implementations, the method further includes estimating, for each locus of a plurality of loci, an average copy number of all alleles (N) at the locus for all cells in the test sample using the genomic sequence data. In some implementations, the initial cancer cell fraction (iCCF) is calculated using VAF, p, and N.

In some implementations, the method further includes obtaining the at least one test sample from an individual; obtaining cellular DNA or cell-free DNA (cfDNA) from the at least one test sample; and sequencing the cellular DNA or the cfDNA to produce the sequence reads.

In some implementations, the method further includes applying a treatment regimen based at least in part on the one or more fCCFs.

In some implementations, applying a treatment regimen includes: comparing the one or more fCCFs for the one or more somatic mutations to one or more criteria or threshold values; and prescribing, initiating, and/or altering a treatment regimen based on the comparison. In some implementations, the treatment regimen affects a biological pathway associated with the one or more somatic mutations. In some implementations, the treatment regimen includes an immunotherapy. In some implementations, the nucleic acid in the at least one test sample includes cfDNA.

In some implementations, the at least one test sample includes two or more test samples from an individual.

In some implementations, the iCCF is calculated based on (VAF*N)/p.

In some implementations, the iCCF is calculated using a copy number of the variant allele of the somatic mutation (n), as well as VAF, p, and N. In some implementations, the iCCF is calculated based on (VAF*N)/(p*n). In some implementations, the iCCF is calculating with an assumption that n is 1. In some implementations, iCCF is calculated based on: (i) (VAF*N)/p when (VAF*N)/p is not larger than 1, and (ii) 1 when (VAF*N)/p is larger than 1.

In some implementations, the clustering includes determining one or more posterior probabilities of a mutation belonging to the one or more clusters. In some implementations, the one or more fCCFs are calculated using the one or more posterior probabilities and the plurality of iCCFs. In some implementations, an fCCF for a mutation is calculated as a linear combination of a mean iCCF of somatic mutations in each cluster and a posterior probability of the mutation belonging to each cluster. In some implementations, $fCCF_m$ for mutation m is calculated using the following formula:

$$fCCF_m = \Sigma_k (\overline{iCCF_k} \times pr_{m,k})$$

wherein $\overline{iCCF_k}$ is the average iCCF of cluster k; and $pr_{m,k}$ is the probability that mutation m belongs to cluster k.

In some implementations, cluster k includes a cluster of a highest probability for the mutation.

In some implementations, the clustering includes using a mixture model to determine the one or more clusters. In some implementations, the mixture model includes a variational Bayesian mixture model. In some implementations, the clustering includes determining a number of subclones giving rise to the one or more clusters of iCCFs. In some implementations, determining a subclone of the number of subclones includes identifying a subset of the plurality of somatic sequence variants that cluster together based on the estimated fractions of the subset all being within a predetermined range. In some implementations, the mixture model includes a mixture of two or more probability distributions of variant allele counts for two or more clusters. In some implementations, each probability distribution of variant allele counts is selected from the group consisting of a binomial distribution, a beta distribution, a Gaussian distribution, and any combinations thereof. In some implementations, each probability distribution of variant allele counts is a binomial distribution. In some implementations, the variant allele count is calculated based on the sequencing depth and an iCCF. In some implementations, the variant allele count is calculated as: variant allele count=depth× iCCF.

In some implementations, iCCF of a mutation is modeled as beta random variable having a beta distribution for a cluster. In some implementations, the at least one test sample includes one sample, and a probability of a mutation belonging to a cluster is modeled as:

$$pr_{m,k} = \text{Beta}(f; u_k, v_k) = \frac{\Gamma(u_k + v_k)}{\Gamma(u_k)\Gamma(v_k)} f^{u_k-1}(1-f)^{v_k-1}$$

Wherein $pr_{m,k}$ is a probability that mutation m belongs to cluster k;

Beta(;) is a probability density function of a beta distribution for cluster k; f is iCCF for mutation m; $\Gamma( )$ is a gamma function; and $u_k$ and $v_k$ are shape parameters of the beta distribution for cluster k.

In some implementations, the at least one test sample includes two or more test samples, and a probability of a mutation belonging to a cluster is modeled as:

$$pr_{m,k} = p(f \mid u_k, v_k) = \text{Beta}(f; u_k, v_k) = \prod_{s=1}^{S} \text{Beta}(f; u_{ks}, v_{ks})$$

wherein $u_k$ and $v_k$ are the shape parameter vectors whose $s^{th}$ components are $u_{ks}$ and $v_{ks}$, respectively.

In some implementations, the plurality of loci includes one or more biallelic loci.

In some implementations, one or more mutations of the plurality of somatic mutations overlap with one or more copy number variations (CNVs).

In some implementations, the method does not assume that all cancer cells are either affected by a CNV or not affected by the CNV. In some implementations, the method does not assume that all cancer cells carrying a somatic mutation are either affected by a CNV or not affected by the CNV.

In some implementations, the clustering does not use Markov chain Monte Carlo (MCMC) methods.

In some implementations, the plurality of somatic mutations includes a mutation selected from the group consisting of a single nucleotide variant (SNV), a an indel, or a combination thereof.

An additional aspect of the disclosure provides a system for estimating one or more CCFs for one or more mutation variants in one or more test samples from a subject. The system includes a sequencer for receiving nucleic acids from the test sample providing nucleic acid sequence information from the sample, a processor; and one or more computer-readable storage media having stored thereon instructions for execution on the processor to estimate one or more CCFs for one or more mutation variants using the methods described herein.

In some implementations, the system includes a tool for extracting nucleic acid molecules from the nucleic acid sample.

An additional aspect of the disclosure provides a computer program product including a non-transitory machine readable medium storing program code that, when executed by one or more processors of a computer system, causes the computer system to estimate one or more CCFs for one or more mutation variants using the methods described herein.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

DETAILED DESCRIPTION

Definitions

Figure 1:
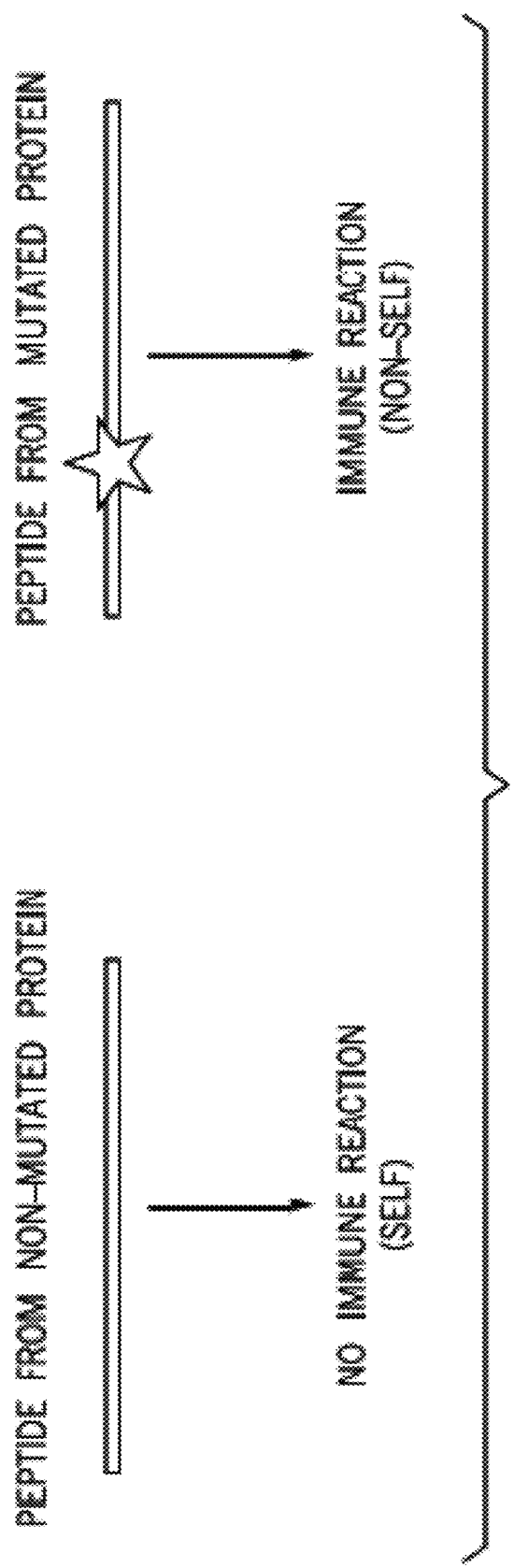
FIG. 1 is a schematic diagram of an example mutated peptide caused by somatic mutation that may occur during cancer progression.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

When the term "about" is used to modify a quantity, it refers to a range from the quantity minus 10% to the quantity plus 10%.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art. As used herein, the singular terms "a," "an," and "the" include the plural reference unless the context clearly indicates otherwise.

The term "mutation" refers to the changing of the structure of a gene, resulting in a variant form that may be transmitted to subsequent generations, caused by the alteration of base units in DNA, or the deletion, insertion, or rearrangement of larger sections of genes or chromosomes.

Mutations include but are not limited to single nucleotide polymorphism (SNP), the mutated variant of which is known as single nucleotide variant (SNV); indel; and copy number variation (CNV). However, the term "mutation" is also used in a narrower sense in some instances to include SNV and indel, but exclude CNV, as apparent from the context distinguishing the former from the latter. Some mutations are known to be associated with cancers. Such mutations are referred to cancer mutation and the corresponding variants are referred to as cancer variants.

A single nucleotide polymorphism (SNP) is a variation in a single nucleotide that occurs at a specific position in the genome, where each variation is present to some appreciable degree within a population (e.g. >1%).

Polymorphism and genetic polymorphism are used interchangeably herein to refer to the occurrence in the same population of two or more alleles at one genomic locus, each with appreciable frequency.

Polymorphism site and polymorphic site are used interchangeably herein to refer to a locus on a genome at which two or more alleles reside. In some implementations, it is used to refer to a single nucleotide variation with two alleles of different bases.

The term "allele" refers to one of two or more alternative forms of a gene and are found at the same locus on a genome.

The term "allele count" refers to the number of sequence reads including a particular allele. In some implementations, it can be determined by mapping reads to a location in a reference genome, and counting the reads that include an allele sequence and are mapped to the reference genome.

Allele frequency is the frequency of an allele of a gene (or a variant of the gene) relative to all alleles of the gene, which can be expressed as a fraction or percentage. An allele frequency is often associated with a particular genomic locus, because a gene is often located at one or more locus.

The term "variant allele" is used herein to refer to an allele of a variant of interest, or more specifically an allele of a cancer related variant.

The term "variant allele frequency" refers to the frequency of the variant allele relative to all alleles.

The term "cancer cell fraction" (CCF) or "cancer cell mutation fraction" refers to a fraction of cancer cells having a variant allele of a somatic mutation among all cancer cells. A CCF may be calculated for one or more samples of a subject. When multiple samples are used, the CCF may be more valid and/or reliable according to some implementation than using a single sample.

Cancer purity refers to refers to the portion of cancer cells relative to all cells in a sample.

Certain somatic mutations occur in a founding cell and pass on to all of the cell's progeny cells. These mutations are referred to as clonal mutations. The growth of progeny cells is referred to as clonal expansion. A population of the progeny cells is referred to as a "clone" or a clonal variety of cells herein. But in another uses, the term "clones" is also used to refer to cells in the population of the progeny cells.

Some somatic mutations are sub-clonal, which occur in an existing neoplastic cell in a cancer clone, and are passed on only to the subpopulation of cells derived from it. The subpopulation of cells is referred to as a "subclone" or a subclonal variety of cells.

"Clustering" or cluster analysis refers to a process of grouping a set of items such a way that items in a same group (called a cluster) are more similar to each other than to those in other groups (clusters) according to certain standards. Clustering can be achieved by various techniques that differ significantly in their understanding of what constitutes a cluster and how to efficiently find them. Popular standards for forming clusters include groups with small distances between cluster members, dense areas of the data space, intervals or particular statistical distributions. Clustering can therefore be formulated as a multi-objective optimization problem. The appropriate clustering algorithm and parameter settings (including parameters such as the distance function to use, a density threshold or the number of expected clusters) depend on the individual data set and intended use of the results. Clustering techniques include but are not limited to: connectivity-based clustering (e.g., hierarchical clustering), centroid-based clustering (e.g., k-means clustering), distribution-based clustering and density-based clustering.

A binomial experiment is a statistical experiment that has the following properties: the experiment consists of n repeated trials; each trial can result in just two possible outcomes (success/failure); the probability of success, denoted by p, is the same on every trial; and the trials are independent. The number of successes X in n repeated trials of a binomial experiment is a binomial random variable.

A binomial random variable can be denoted as $X \sim B(n,p)$ or $X \sim BN(n, p)$.

The probability distribution of a binomial random variable is called a binomial distribution. For a single experiment, i.e., n=1, the binomial distribution is a Bernoulli distribution. The binomial distribution has the following properties: the mean of the distribution is $\mu=n*p$; the variance is $\sigma^2=n*p*(1-p)$; and the standard deviation is $\sigma=\text{sqrt}[n*P*(1-P)]$.

The binomial probability refers to the probability that a binomial experiment results in exactly x successes. The binomial probability can be calculated as follows.

$$pr = BN(x;n,p) = C_x^n \times p^x \times (1-p)^{n-x}$$

A beta distribution is a family of continuous probability distributions defined on the interval [0, 1] parameterized by two positive shape parameters, denoted by, e.g., $\alpha$ and $\beta$ (or u and v), that appear as exponents of the random variable and control the shape of the distribution. The beta distribution has been applied to model the behavior of random variables limited to intervals of finite length in a wide variety of disciplines. In Bayesian inference, the beta distribution is the conjugate prior probability distribution for the Bernoulli, binomial, negative binomial and geometric distributions. For example, the beta distribution can be used in Bayesian analysis to describe initial knowledge concerning probability of success.

If the probability distribution of a random variable X is beta distribution, the random variable X is referred to as a beta random variable. A beta random variable can be denoted as $X \sim \text{Beta}(\alpha, \beta)$ or $X \sim \beta(\alpha, \beta)$.

The beta probability refers to the probability that a beta random variable having the value of x. The beta probability can be calculated as follows.

$$pr = \text{Beta}(x; \alpha, \beta) = \frac{\Gamma(\alpha+\beta)}{\Gamma(\alpha)\Gamma(\beta)} x^{\alpha-1}(1-x)^{\beta-1}$$

wherein Beta(x; $\alpha$, $\beta$) is a probability density function of beta distribution Beta($\alpha$, $\beta$), and $\Gamma(\ )$ is a gamma function.

Circulating cell-free DNA or simply cell-free DNA (cfDNA) are DNA fragments that are not confined within cells and are freely circulating in the bloodstream or other bodily fluids. It is known that cfDNA have different origins, in some cases from tumor cells or tumor affected cells, in other cases from fetal DNA circulating in maternal blood. In general, cfDNA are fragmented and include only a small portion of a genome, which may be different from the genome of the individual from which the cfDNA is obtained.

The term non-circulating genomic DNA (gDNA) or cellular DNA are used to refer to DNA molecules that are confined in cells and often include a complete genome.

The term "read" refers to a sequence obtained from a portion of a nucleic acid sample. Typically, though not necessarily, a read represents a short sequence of contiguous base pairs in the sample. The read may be represented symbolically by the base pair sequence (in A, T, C, or G) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "parameter" is used herein represents a physical feature whose value or other characteristic has an impact a relevant condition such as copy number variation. In some cases, the term parameter is used with reference to a variable that affects the output of a mathematical relation or model, which variable may be an independent variable (i.e., an input to the model) or an intermediate variable based on one or more independent variables. Depending on the scope of a model, an output of one model may become an input of another model, thereby becoming a parameter to the other model.

The term "copy number variation" herein refers to variation in the number of copies of a nucleic acid sequence present in a test sample in comparison with the copy number of the nucleic acid sequence present in a reference sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a nucleic acid sequence of interest in test sample with an expected level of the nucleic acid sequence of interest. For example, the level of the nucleic acid sequence of interest in the test sample is compared to that present in a qualified sample. Copy number variants/variations include deletions, including microdeletions, insertions, including microinsertions, duplications, multiplications, and translocations. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The term "plurality" refers to more than one element. For example, the term is used herein in reference to a number of nucleic acid molecules or sequence tags that are sufficient to identify significant differences in copy number variations in test samples and qualified samples using the methods disclosed herein. In some embodiments, at least about $3 \times 10^6$ sequence tags of between about 20 and 40 bp are obtained for each test sample. In some embodiments, each test sample provides data for at least about $5 \times 10^6$, $8 \times 10^6$, $10 \times 10^6$, $15 \times 10^6$, $20 \times 10^6$, $30 \times 10^6$, $40 \times 10^6$, or $50 \times 10^6$ sequence tags, each sequence tag comprising between about 20 and 40 bp.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The term "test sample" herein refers to a sample, typically derived from a biological fluid, cell, tissue, organ, or organism, comprising a nucleic acid or a mixture of nucleic acids comprising at least one nucleic acid sequence that is to be analyzed in a test. In certain embodiments the sample comprises at least one nucleic acid sequence. Such samples include, but are not limited to, hard and soft tissues, sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used to test samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "training set" herein refers to a set of training samples that can comprise affected and/or unaffected samples and are used to develop a model for analyzing test samples. In some embodiments, the training set includes unaffected samples. In these embodiments, thresholds for determining CNV are established using training sets of samples that are unaffected for the copy number variation of interest. The unaffected samples in a training set may be used as the qualified samples to identify normalizing sequences, e.g., normalizing chromosomes, and the chromosome doses of unaffected samples are used to set the thresholds for each of the sequences, e.g., chromosomes, of interest. In some embodiments, the training set includes affected samples. The affected samples in a training set can be used to verify that affected test samples can be easily differentiated from unaffected samples.

A training set is also a statistical sample in a population of interest, which statistical sample is not to be confused with a biological sample. A statistical sample often comprises multiple individuals, data of which individuals are used to determine one or more quantitative values of interest generalizable to the population. The statistical sample is a subset of individuals in the population of interest. The individuals may be persons, animals, tissues, cells, other biological samples (i.e., a statistical sample may include multiple biological samples), and other individual entities providing data points for statistical analysis.

Usually, a training set is used in conjunction with a validation set. The term "validation set" is used to refer to a set of individuals in a statistical sample; data of which individuals are used to validate or evaluate the quantitative values of interest determined using a training set. In some embodiments, for instance, a training set provides data for calculating a mask for a reference sequence, while a validation set provides data to evaluate the validity or effectiveness of the mask.

"Evaluation of copy number" is used herein in reference to the statistical evaluation of the status of a genetic sequence related to the copy number of the sequence. For example, in some embodiments, the evaluation comprises the determination of the presence or absence of a genetic sequence. In some embodiments the evaluation comprises the determination of the partial or complete aneuploidy of a genetic sequence. In other embodiments the evaluation comprises discrimination between two or more samples based on the copy number of a genetic sequence. In some embodiments, the evaluation comprises statistical analyses, e.g., normalization and comparison, based on the copy number of the genetic sequence.

The term "coverage" refers to the abundance of sequence tags mapped to a defined sequence. Coverage can be quantitatively indicated by sequence tag density (or count of sequence tags), sequence tag density ratio, normalized coverage amount, adjusted coverage values, etc.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a property of a system. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation, e.g., an aneuploidy, in an organism. If a threshold is exceeded by results obtained from methods disclosed herein, a subject can be diagnosed with a copy number variation, e.g., trisomy 21. Appropriate threshold values for the methods described herein can be identified by analyzing normalized values (e.g. chromosome doses, NCVs or NSVs) calculated for a training set of samples. Threshold values can be identified using qualified (i.e., unaffected) samples in a training set which comprises both qualified (i.e., unaffected) samples and affected samples. The samples in the training set known to have chromosomal aneuploidies (i.e., the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may be advantageous to use larger sets of qualified samples to improve the diagnostic utility of the threshold values.

The term "bin" refers to a segment of a sequence or a segment of a genome. In some embodiments, bins are contiguous with one another within the genome or chromosome. Each bin may define a sequence of nucleotides in a reference sequence such as a reference genome. Sizes of the bin may be 1 kb, 100 kb, 1 Mb, etc., depending on the analysis required by particular applications and sequence tag density. In addition to their positions within a reference sequence, bins may have other characteristics such as sample coverage and sequence structure characteristics such as G-C fraction.

The term "read" refers to a sequence obtained from a portion of a nucleic acid sample. Typically, though not necessarily, a read represents a short sequence of contiguous base pairs in the sample. The read may be represented symbolically by the base pair sequence (in A, T, C, or G) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to allow a limited amount of mismatch in aligning to a reference genome. In some embodiments, tags that can be mapped to more than one location on a reference genome, i.e., tags that do not map uniquely, may not be included in the analysis.

The term "locus" or "site" refers to a unique position (i.e. chromosome ID, chromosome position and orientation) on a reference genome. In some embodiments, a site may provide a position for a residue, a sequence tag, or a segment on a sequence.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "mapping" used herein refers to specifically assigning a sequence read to a larger sequence, e.g., a reference genome, by alignment.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "sensitivity" as used herein refers to the probability that a test result will be positive when the condition of interest is present. It may be calculated as the number of true positives divided by the sum of true positives and false negatives.

The term "specificity" as used herein refers to the probability that a test result will be negative when the condition of interest is absent. It may be calculated as the number of true negatives divided by the sum of true negatives and false positives.

Introduction and Context

The present techniques provide a novel approach for inference of clonality of somatic mutations from sequencing data. In contrast to other techniques, which take hours to analyze a set of hundreds of somatic mutations, the disclosed techniques infer the clonality of hundreds to thousands of somatic mutations in under one minute, saving substantial computer resources. Further, the disclosed techniques display similar accuracy to existing methods. An additional advantage of the disclosed techniques is that the loss in accuracy when inferring clonality of somatic mutations from a single tumor sample, as opposed to multi-site sampling from the same tumor, is reduced relative to existing methods.

Figure 2:
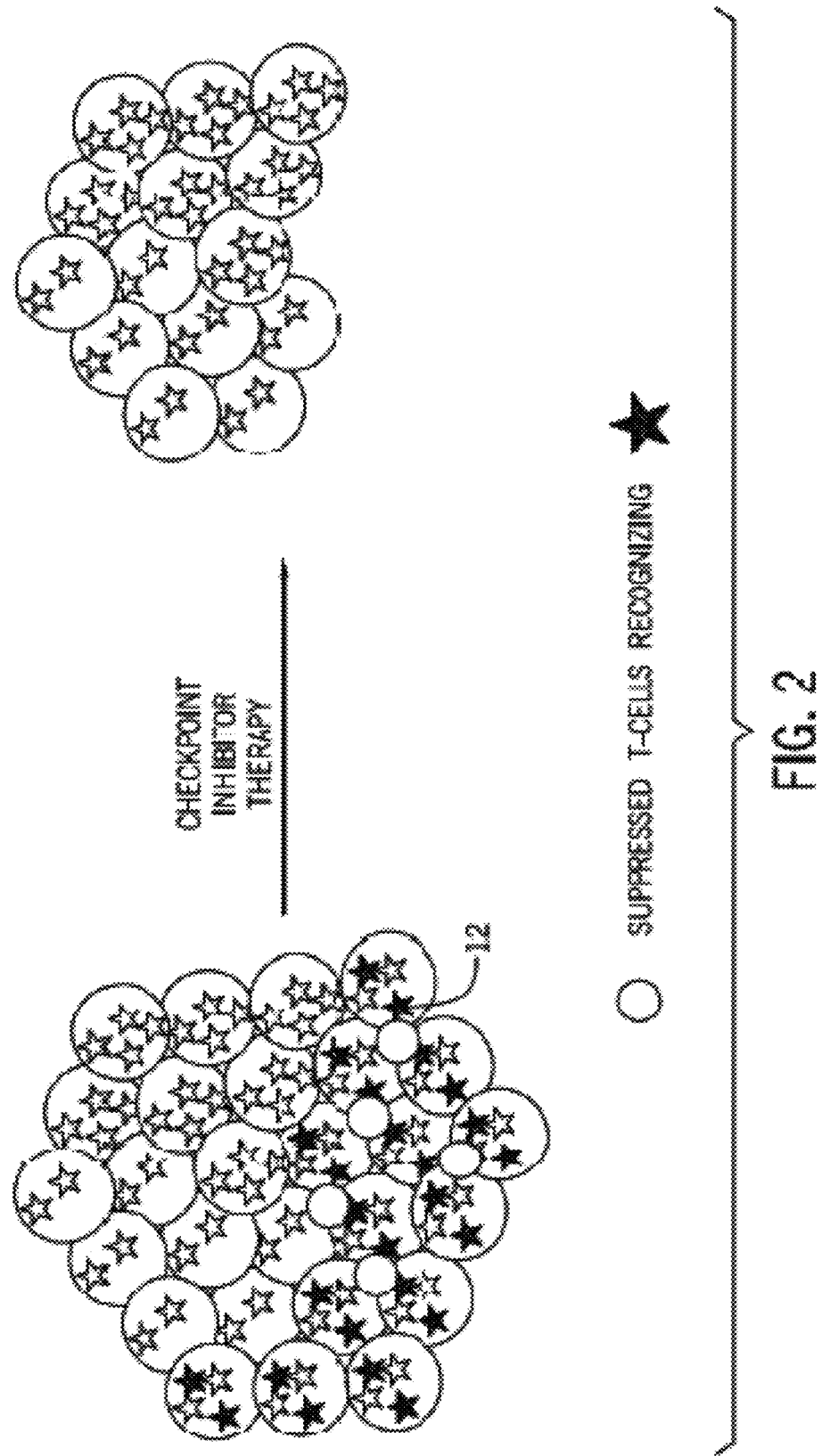
FIG. 2 is a schematic illustration of checkpoint inhibitor therapy as applied to a tumor with a subclonal neoantigen expression.

The present techniques may be implemented as part of a neoantigen prediction and prioritization pipeline. FIG. 1 is a schematic diagram of an example mutated peptide caused by somatic mutation that may occur during cancer progression. The mutated peptide may generate an immune reaction to the mutated peptide neoantigen, which is exploited by immune therapies that target cells expressing neoantigens. Such therapies may include checkpoint inhibitor therapies as well as vaccine-based therapies that are customized to the set of neoantigens expressed by a patient. Because such therapies are costly and may be complex to administer, it would be beneficial to determine which patients are likely to experience improvements from undergoing immune-based therapies. It has been demonstrated that success of immune therapies that rely on neoantigen targeting may depends on the prevalence of the neoantigens within the population of tumor cells, and that the clonality of neoantigens is a significant factor in segregating responders from non-responders to checkpoint inhibitor therapy. FIG. 2 is a schematic illustration of checkpoint inhibitor therapy as applied to a tumor with a subclonal neoantigen expression. The suppressed T-cells targeting the neoantigen 12 are activated in response to the checkpoint inhibitor therapy. However, because the neoantigen 12 is not expressed in all tumor cells in the tumor, the therapy only targets a subset of the tumor cells, which in turn result in incomplete tumor targeting and unsuccessful therapy, as tumor cells not expressing the neoantigen 12 are unaffected by the T-cells.

The present techniques provide improvements in the prediction of the population of tumor cells that exhibit neoantigen expression and in the characterization of the particular neoantigens associated with a given tumor sample without the need for significant increase in the total run time of the workflow. Such predictions may prevent administration of immune-based therapies to patients having tumors unlikely to respond to such therapies. In addition, because cancer progresses over time, a tumor of an individual patient may be monitored to determine if a patient previously not considered a candidate for immune-based therapies has a change in tumor status that renders the patient more likely to respond to immune-based therapies. While previous techniques involve resource-intensive calculations to infer the clonality of somatic mutations, the disclosed novel approaches permit accurate inference of clonality in a matter of minutes rather than hours, making such determinations more clinically accessible.

Figure 3:
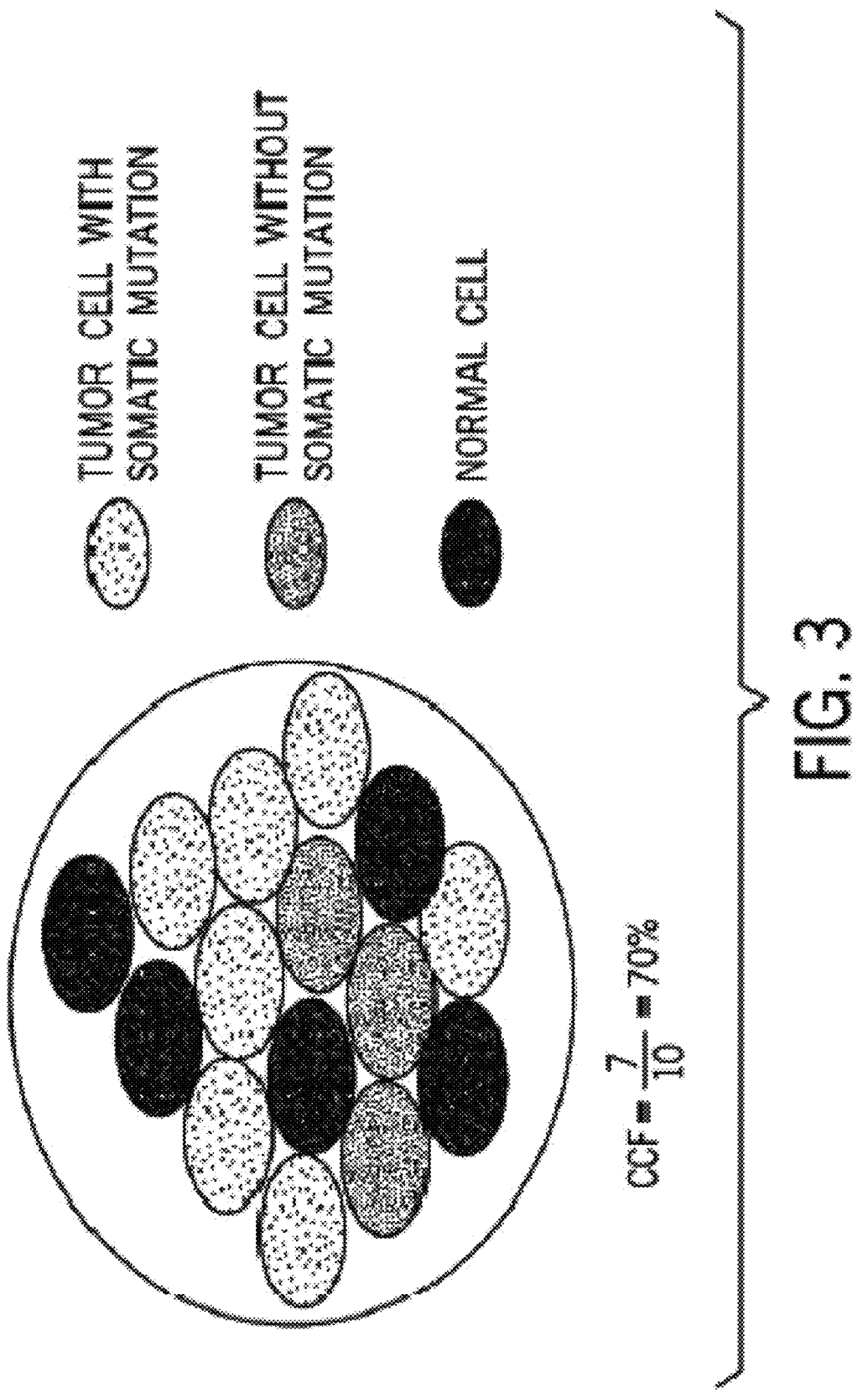
FIG. 3 is a schematic illustration of a tumor that includes normal cells and a heterogeneous mixture of tumor cells with a particular somatic mutation and tumor cells without the particular somatic mutation.

FIG. 3 is a schematic illustration of a tumor that includes normal cells and a heterogeneous mixture of tumor cells with a particular somatic mutation and tumor cells without the particular somatic mutation. It should be understood that the illustrated example is applied to a single somatic mutation, and that other somatic mutations may have different distributions within a sample. Further, the mixture of normal and tumor cells in the sample may be different for a sample taken from a different site in the tumor. The cancer cell fraction of the somatic mutation in the illustrated example is 70%, and is based on the percentage of tumor cells, and not normal cells, including the somatic mutation.

Figure 4:
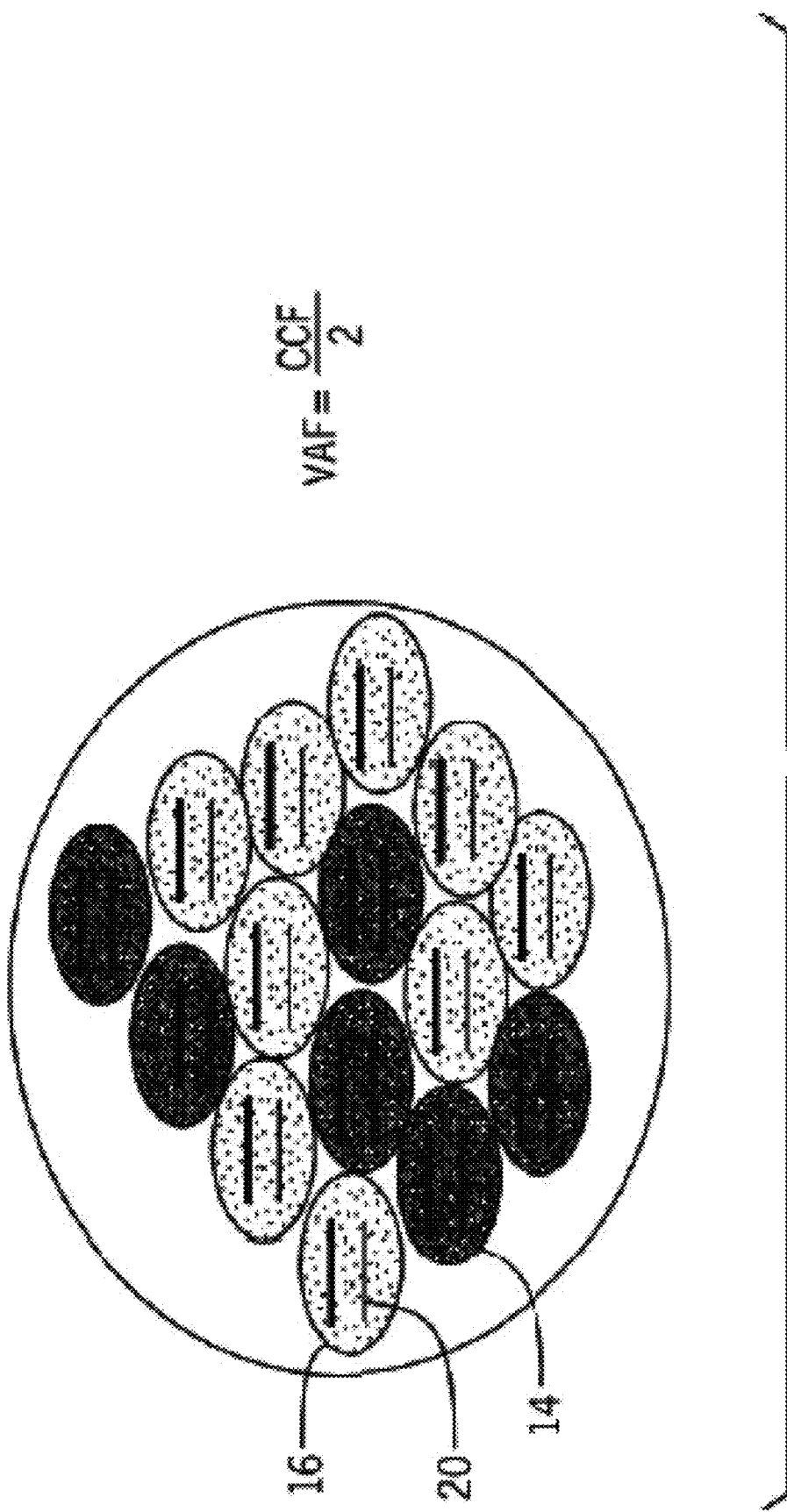
FIG. 4 shows a schematic example in which all of the normal cells and tumor cells include one copy of a somatic mutation.

As the fraction of cells affected by a somatic mutation increases, the expected fraction of sequence reads mapping to the mutated locus and displaying that mutation, the variant allele frequency (VAF), will also increase. In the case when a sample is made up of only tumor cells, and a somatic mutation affects only one of the two alleles, the CCF is simply twice the expected variant allele frequency, as shown in the example of FIG. 4 in which all of the normal cells 14 and tumor cells 16 include one copy of the somatic mutation, indicated as a variant allele 20. That is, when the variant allele frequency is 0.5 (indicative of 50% of sequence reads including the sequence variant), the CCF is 1 (indicative of the variant allele being present in 100% of cells in the sample).

Figure 5:
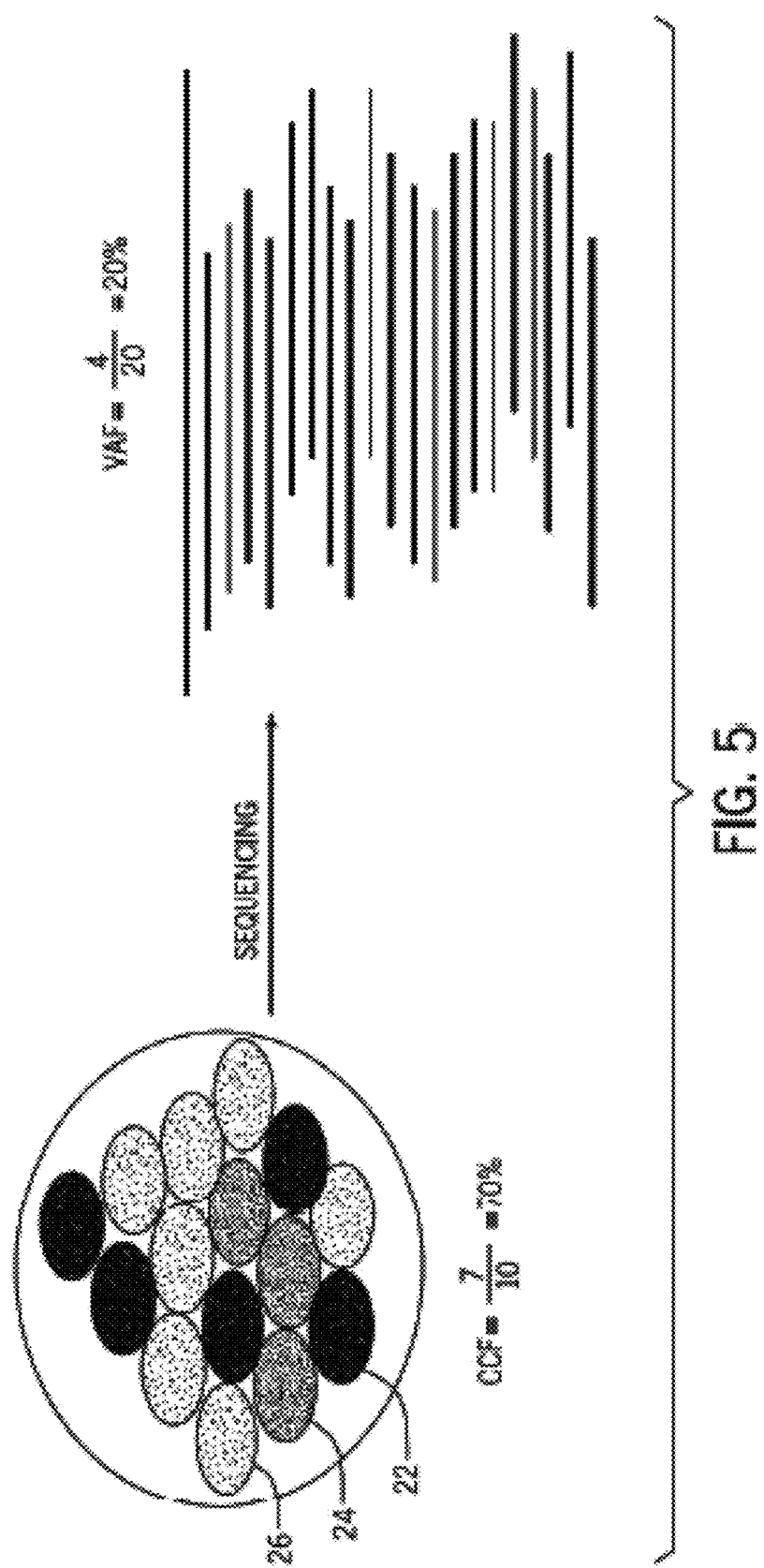
FIG. 5 shows a schematic example in which the tumor sample is not made up of only tumor cells, but also of normal cells.

However, tumor samples are not made up of only tumor cells, but also of normal cells 22, as shown in the example of FIG. 5. Further, tumor cells in a tumor sample may be heterogeneous, including cells that diverge from one another and that have different characteristic somatic mutations. Accordingly, the tumor includes a mixture of cells 24 that don't include a particular somatic mutation and cells 26 that do include the particular somatic mutation. Further, when a second (or a different) somatic mutation is considered, the mixture may change, with the cells 24 having the second mutation and the cells 26 not including the second mutation. For clonal populations, certain somatic mutations will be inherited together such that identification of somatic mutations found in similar fractions of tumor cells may be considered to be part of a same subclone as provided herein. In one embodiment, individual somatic mutations having a cancer cell fraction within plus or minus 5% relative to another cancer cell fraction of another somatic mutation may be considered likely to be part of the same subclone. That is, if a somatic mutation has a cancer cell fraction of x %, other somatic mutations have cancer cell fractions in a range of x−5% to x+5% may be considered to be likely to be part of a same subclone. In other embodiments, somatic mutations that are part of a same subclone may be identified via clustering analysis as provided herein.

Figure 6:
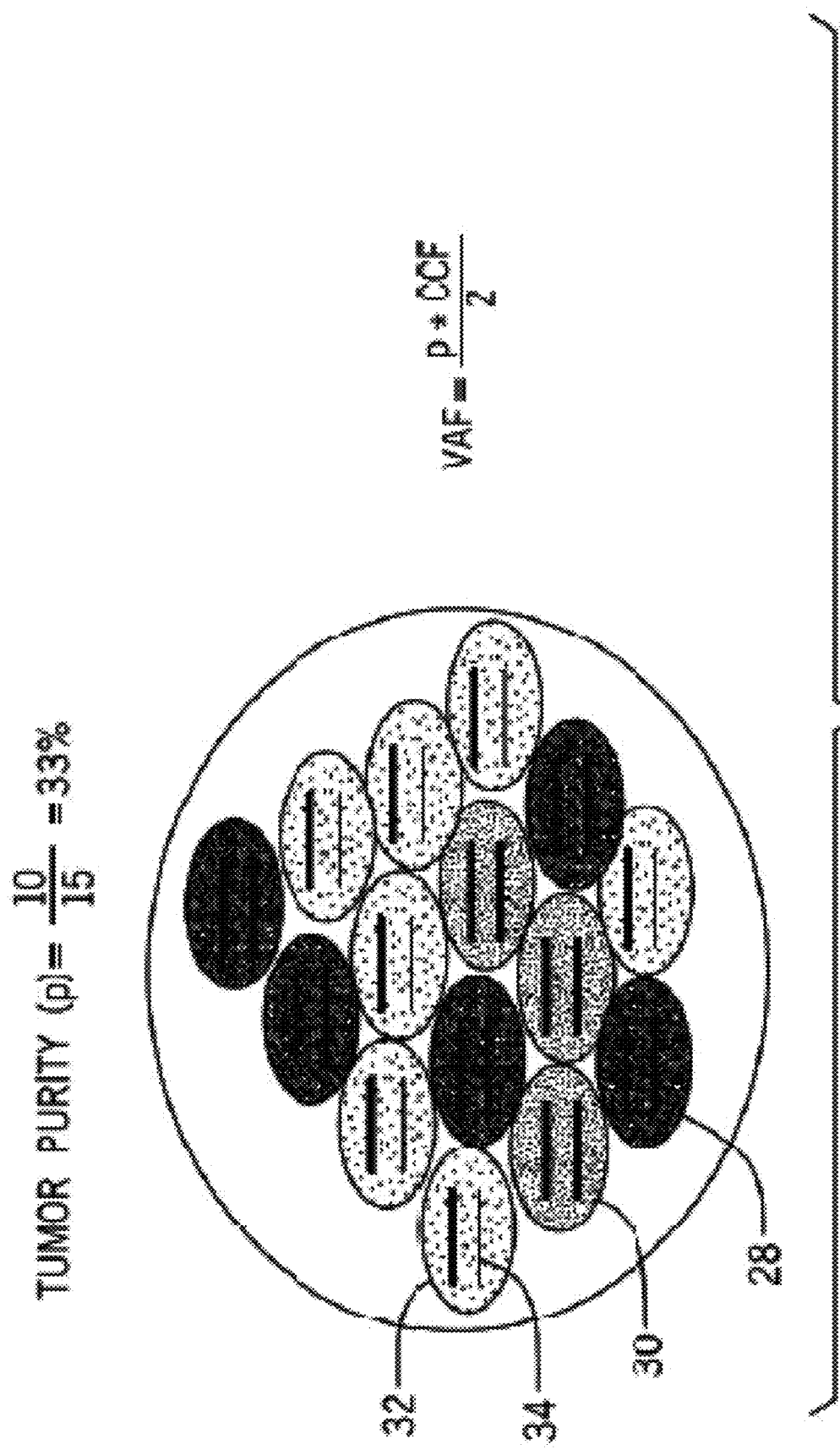
FIG. 6 shows a schematic example for a tumor with 5 nontumor cells and 10 tumor cells.

FIG. 5 shows that the VAF for the example somatic mutation having a CCF of 70% is 20%, which is reflective of the sample including nontumor cells as well as tumor cells not having the somatic mutation. In such a case, the variant allele frequency is a function of the tumor purity (p) and the cancer cell fraction. As shown in FIG. 6, for a tumor with 5 nontumor cells 28 and 10 tumor cells, the tumor cells including a mixture of cells without a somatic mutation 30 and cells with the somatic mutation 32, the somatic mutation being indicated as a variant allele 34, the tumor purity (p) is expressed as 33%.

Figure 7:
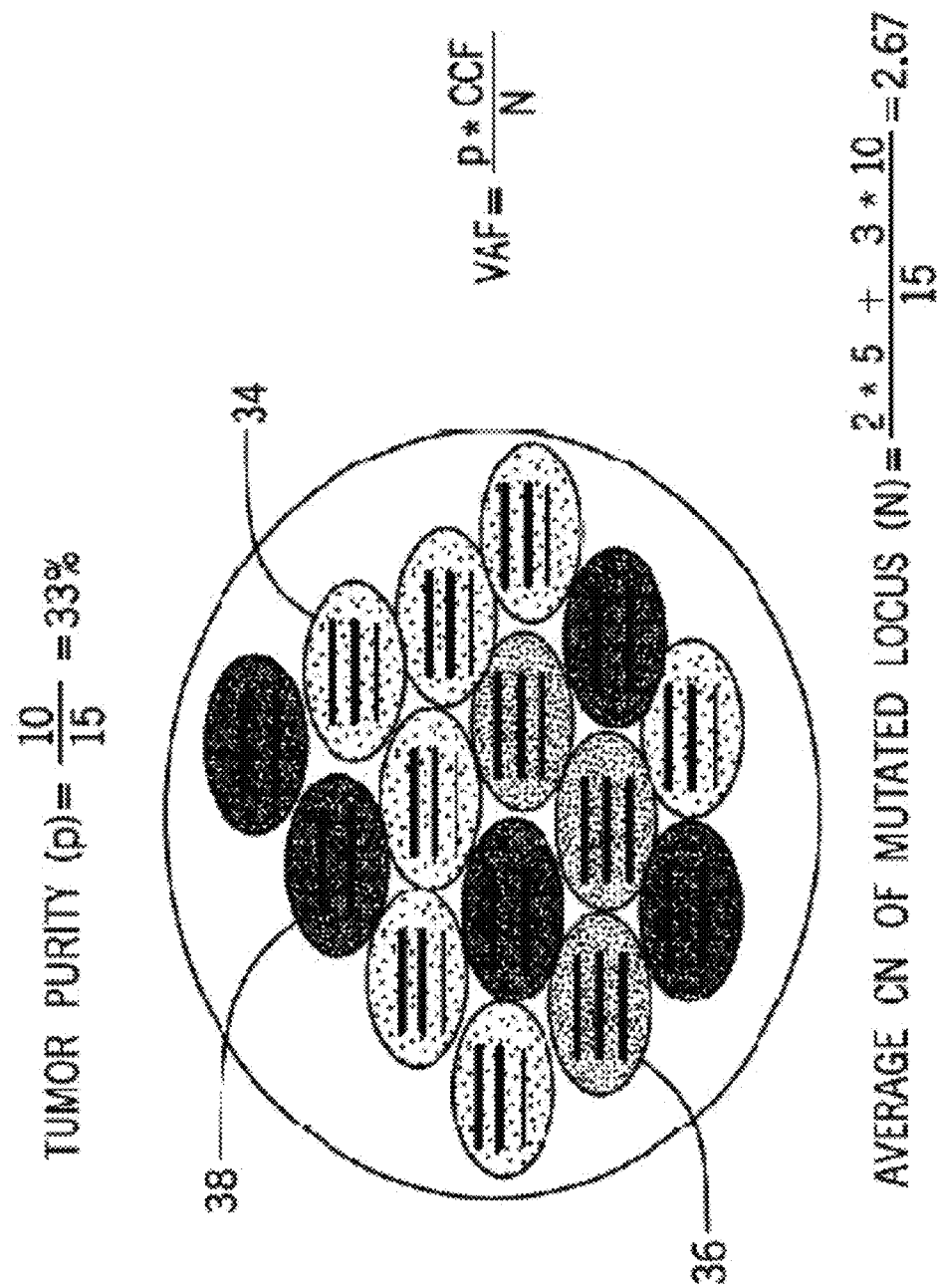
FIG. 7 shows a schematic example in which the locus that includes the somatic mutation in only some of the tumor cells has a gain in copy number in the nonvariant alleles relative to the normal cells.
Figure 8:
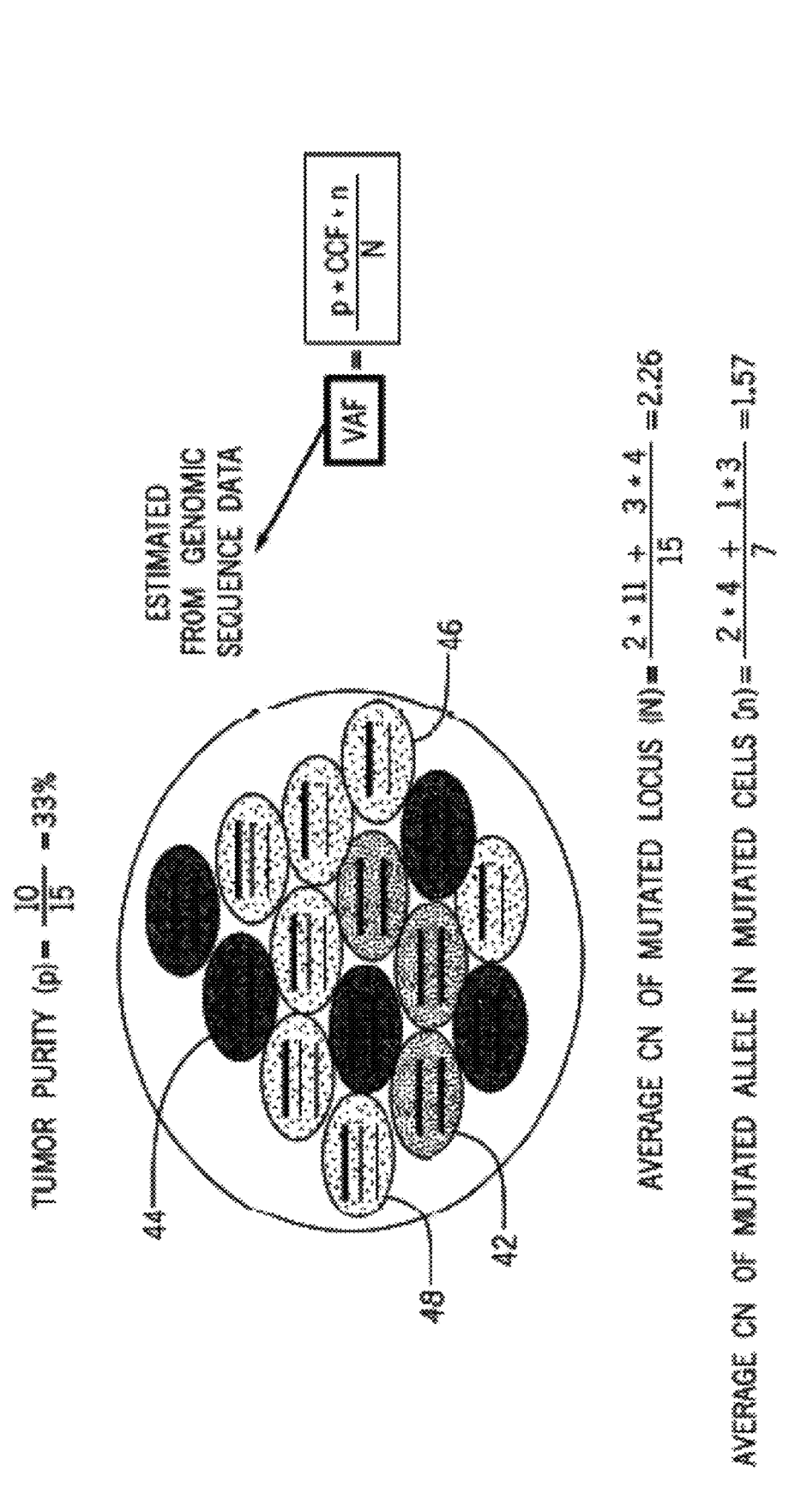
FIG. 8 shows an illustrative example where CNVs is subclonal, and they affect the same or different set of tumor subclones as the somatic mutation.

However, this does not account for copy number variations in the tumor cells that can also influence the relationship between the expected VAF and the cancer cell fraction. FIG. 7 shows an example in which the locus that includes the somatic mutation in only some of the tumor cells has a gain in copy number in the nonvariant alleles relative to the normal cells. That is, the somatic mutation, as shown in tumor cell 34, is subclonal while the copy number gain in the nonvariant allele is across the population of tumor cells, including tumor cells 36 that do not include the somatic mutation, relative to normal cells 38. Further, CNVs can be subclonal, and they may affect the same or different set of tumor subclones as the somatic mutation, as shown in the example of FIG. 8. Certain CNVs affect the allele carrying the mutation, while other CNVs affect the other allele. As shown in the illustrated example, one population of tumor cells 42 exhibits a similar phenotype with regard to the CNV and the somatic mutation as the normal cells 44. Another population of tumor cells 46 includes the somatic mutation but not the CNV, while yet another population of tumor cells 48 includes both the CNV and the somatic mutation. With all that, a general relationship between the expected VAF and CCF can be written as:

$$VAF = \frac{p * CCF * n}{N}$$

where p is the tumor purity, n is the average number of mutated copies of that genomic locus in cells that carry the mutation, and N is the average copy number of that genomic locus across all cells in the sample and p, n, N, and CCF are all unknown quantities.

The observed VAF is an estimate of the expected VAF (for which the relationship to CCF holds). As the sequencing depth increases, the observed VAF becomes closer to the expected VAF. Therefore, a higher depth will usually lead to better CCF estimates. However, in certain embodiments, the variability in the observed VAF may be addressed using information across all somatic mutations that are present in the same tumor subclones. If multiple somatic mutations are present in the same tumor subclones, they will by definition have the same CCF (and same expected VAF if they don't overlap CNVs).

It is unknown which somatic mutations belong to the same tumor subclones or how many subclones can be found in a particular tumor. However, by clustering somatic mutations based on their VAF or CCF, the number of tumor subclone can be estimated, and the final CCF estimate for all mutations within each cluster can be assigned as the mean (or other statistic) CCF for that cluster.

Somatic mutations may be clustered based on a single sample. However, clustering is more reliable if multiple samples from the same tumor are available. When multiple samples are available, it is expected that mutations from the same subclone will consistently have the same cancer cell fraction across all samples (co-variation). Therefore, when such pattern of covariation is observed, variants may more reliably be clustered together.

The present techniques provide advantages over existing methods that make some kind of simplifying assumption in order to estimate CCF from VAF. Drawbacks of these methods include inaccuracies due to disregarding the effects of various scenarios of CNVs and variability in tumor purity. Further, certain techniques do not account for inaccuracies in estimated caused by somatic mutations that overlap CNVs. Because often a very large fraction of the somatic mutations within a tumor overlap CNVs.

Another common assumption is that CNVs are clonal. Methods that make that assumption also assume that the copy number of the CNV-affected locus in tumor cells and the tumor purity were accurately estimated by a previously run CNV calling tool. When such assumptions are satisfied, N will be estimated as:

$$N = p*C + (1-p)*2$$

where C is the copy number of that locus on all tumor cells. In that case, n can also only assume a limited number of integer values between 1 and C, or an even smaller number of possible values when allelic copy number values are available. Such methods will try to determine which values of n and CCF are most likely to lead to the observed VAF. A variation on the clonal CNV assumption made by certain methods is that CNVs are not necessarily clonal, but that all cells that carry the somatic mutation are either affected or not affected by the CNV (CNV cannot affect only a portion of the cells carrying the mutation). Even though this may address drawbacks of other methods, most CNV calling tools also assume that CNVs are clonal when estimating the copy number of a CNV region, so the benefit that could come from the more complex model may not be that pronounced. Inference of number of tumor subclones, and which mutations belong to the same subclone is sometimes done simultaneously to the inference of the other parameters using Markov chain Monte Carlo analysis or related methods, and can potentially assist in determining the most likely CCF, and n values across the full set of somatic mutations. The downside of such approaches is the time necessary to complete the analysis.

The present techniques address the deficiencies of other methods that do not accurately address CNV complexity in a tumor sample without concurrently adding complex computational burden. Accordingly, provided is an efficient inference of clonality of somatic mutations that is executed more quickly and using a lower computational load such that a device using the present techniques operates more efficiently.

The present techniques address the issue of CNV complexity by assuming that only one copy of the mutated allele is present in each cell that carries that mutation (n=1). That assumption will hold for all somatic variants that do not overlap CNVs, that overlap a copy number loss, or that overlap a copy number gain that did not specifically affect the mutated allele. With that, the relationship between CCF and the expected VAF becomes:

$$VAF = \frac{p * CCF}{N}$$

where p is the tumor purity, and N is the average copy number of that genomic locus across all cells in the sample. The estimates of p and N are made by a CNV caller, such as the Canvas caller (Illumina, Inc.) in the tumor-normal-enrichment mode. Canvas is an algorithm for calling copy number variants from either (a) a mostly diploid germline sample, or (b) a germline sample together with a tumor sample from the same individual. The vast majority of normal germline samples will be diploid, that is, having two copies. However, tumor samples may be much more extensively rearranged. Canvas identifies regions of the sample's genome that are present in zero, one, or more than two times in the genome. Briefly, this is achieved by scanning the genome for regions that have an unexpected number of short read alignments. Regions with fewer than the expected number of alignments are classified as losses. Regions having more than the expected number of alignments are classified as gains. This analysis is then used to estimate copy number variation at individual loci. Rather than using integer copy number estimates, the present techniques use normalized coverage estimates, which estimate the average copy number of that genomic locus across all cells in the sample (N). The advantage of using the real valued normalized coverage is that this addresses deficiencies in other techniques that assumes clonality of the CNV. With that, as long as the initial assumption holds, the CCF estimates generated by the present techniques will be valid for variants overlapping both clonal and subclonal CNVs.

When n>1, CCF estimates made by the present techniques would potentially be larger than 1. To avoid such nonsensical CCF estimates, the CCF estimate is capped at 1. Therefore, initial CCF estimates are made using the following formula:

$$CCF = \begin{cases} c \text{ if } c < 1 \\ 1 \text{ if } c > 1 \end{cases} \quad c = \frac{VAF * N}{p}$$

Once the initial CCF values are estimated, a SciClone R package was used to cluster somatic mutations based on their CCF. SciClone clusters somatic variants lying outside of CNV regions based on their VAF. Its use of variational Bayesian mixture models for clustering allow for simultaneous clustering and inference of number of clusters, and is significantly more efficient than stochastic Markov chain Monte Carlo techniques used by other methods. However, the present techniques clustered somatic variants based on CCF (normalized for copy number) instead of VAF, which allows clustering of CNV-overlapping somatic variants. SciClone also allows clustering both within a single sample, and across multiple samples of the same tumor. As provided herein, the clustering may be implemented using a variety of different mixture models, including binomial, beta or gaussian mixture models. Such probabilistic clustering leads to a generated output of probability estimates of an individual sequence variant (representative of a somatic mutation) belonging to each of the different clusters. In certain embodiments, the present techniques update the CCF estimates post-clustering to a linear combination of a mean CCF of somatic mutations in each cluster and a posterior probability of the mutation belonging to each cluster. When using binomial mixture modes for clustering, which depend on the actual sequencing depth and count of alternative alleles, the alternative allele counts are adjusted in a way that makes them consistent with the CCF instead of the VAF (alt. counts=depth×ccf).

Technical Problems and Technological Improvements

To effectively treat cancers, it is important to understand not only the mutations underlying cancers but also the clonal architecture of the mutations. A number of parameters relating to the clonal architecture of cancers are useful for designing therapies. For example, cancer cell fractions and the number of subclones are important measures of cancer clonality. One way to determine these parameters is to use single cell sequencing methods to determine the mutations of individual cells in a cancer sample. Based on the genetic information of individual cells, one can determine the clonal structure of the cancer cells. However, single cell sequencing methods have various limitations. At the present time, single cell sequencing is expensive and cannot be performed efficiently to examine a large number of cancer cells. And technical challenges as such as allele dropout remain when using single cell sequencing methods.

One can directly measure variant allele frequency of cancer variants using sequencing data of multiple cells. However, the direct measurement of variant allele frequencies does not provide information about certain clonal structure of the mutations. Cancer cell fraction (CCF) not only relates to variant allele frequency, but also takes into consideration copy number variation and tumor purity, providing more information about the characteristics of cancer mutations. However, cancer cell fraction of an individual mutation has limited sequencing depth, which renders the observed or measured cancer cell fraction noisy and unreliable.

The observed VAF or CCF is an estimate of the expected VAF or expected CCF. As the sequencing depth increases, the observed values become closer to the expected values. So by increasing sequencing depth one can increase the reliability of the observed values. However, such as an approach requires more time, material, and cost to realize the increased sequencing depth. Some existing methods attempt to improve reliability of results by aggregating measurements of mutations that exist in a subclone. The cells of a subclone are supposed to have the same mutations and thus the same CCF. However, these methods include various technical limitations. For example, the widely used method PyClone uses Markov chain Monte Carlo (MCMC) simulation techniques. However, MCMC techniques are computationally demanding and rely on assumptions about chain convergence that introduces uncertainty. Moreover, the method does not properly account for copy number variations that that partially overlap with mutations.

Other methods using copy number to infer clonality avoid computational overhead by making the simplifying assumption that the tumor sample does not harbor sub-clonal copy number events. Such assumption is often untrue. Some methods simply ignore the effect of CNV and tumor purity completely, or do not deal with somatic mutations that overlap CNVs. They focus instead on the problem of determining which somatic mutations belong to the same subclone, namely clustering. These existing methods are undesirable because a very large fraction of the somatic mutations within the tumor overlap CNVs. Many methods assume that CNVs are clonal. However, as explained above, CNVs are not always clonal.

A variation on the clonal CNV assumption, made by PyClone, the widely used tool, is that CNVs are not necessarily clonal, but that all cells carrying the somatic mutation are either affected or not affected by the CNV. Roth et al., (2014), Nat Meth 11: 396-398. In other words, it assumes that CNV cannot affect only a portion of the cells carrying the mutation. This assumption is still not always true and can lead to inaccuracy in CCF or variant allele frequency (VAF) estimates.

One existing method, SciClone, uses the variational mixture model to determine variant allele frequency by clustering VAFs and determining the probabilities of variants belonging to one or more clusters. However, the clustering of SciClone does not account for the average copy number at the mutation locus, the copy number of the variant allele, or the tumor purity level. Miller, et al. (2014), PLoS Comput Biol 10(8): e1003665.

As the fraction of cancer cells affected by a mutation increases (CCF), the expected fraction of reads mapping to the mutation locus and displaying the mutation (VAF) also increases. In the case when a sample is made up of only tumor cells and the somatic mutation affects only one of the two alleles, the CCF is simply twice the expected variant allele frequency. However, tumor samples include not only tumor cells, but also normal cells. Also, copy number variations can influence the relationship between the expected VAF and CCF. Further, CNVs may affect the same or different set of tumors or clones as the somatic mutation. They sometimes affect the allele carrying the mutation, and sometimes the other allele. With all that, a general relationship between the expected VAF and CCF can be written as:

$$VAF = \frac{p * CCF * n}{N}$$

where p is the tumor purity, n is the average number of mutated copies of that genomic locus in cells that carry the mutation, and N is the average copy number of that genomic locus across all cells in the sample. Methods such as SciClone that measure and cluster VAF do adequately account for tumor purity or copy number variations.

Some implementations of the disclosure provides methods and systems for estimating CCF and evaluating clonality of cancer cells, while addressing various shortcomings of existing methods. Implementations of the disclosure aggregate information from multiple mutations in a subclone to increase the reliability of the estimated CCF. Implementations of the disclosure can increase the accuracy of the measures without increasing sequencing depth by aggregating data from somatic mutations in the same subclone. It is not known a priori which somatic mutations belong to the same tumor subclone or how many subclones can be found in that tumor. Implementations of the disclosure use clustering methods to cluster somatic mutations based on their CCFs. The disclosed implementations cluster CCFs instead of VAFs, taking into consideration tumor purity and copy numbers of mutant variants and mutation loci. The disclosed implementations then determine the final CCF for a mutation based on the mean (or other statistical average) of CCF values for the cluster to which the mutation belongs.

Unlike PyClone, the disclosed implementations do not rely on MCMC, thus reducing uncertainty and increasing computational speed. In some implementations, the methods achieve and obtain results in seconds, while existing methods using MCMC techniques obtain results in seven hours.

It is well known that MCMC requires a large amount of computer memory to perform. The disclosed methods not using MCMC can greatly reduce the required computer memory to perform the task.

In an online publication, Guilhoto illustrates that for a two-dimensional example analyzed using MCMC, if one divides each dimension into 500 divisions, this would result in a state space of size 500^2=250000, and a transition matrix with a total of 12500000000 entries. Assuming each entry is stored using 4 bytes of memory (an underwhelming estimate), this would mean that the entire matrix would require 250 GB of memory. For n dimensions, each divided into m partitions, the amount of memory required would be $O(m^{2n})$.

Such computer memory requirements are resource demanding. One work around to reduce the required computer memory is to calculated any specific transition probability each time it was required, rather than storing all values in memory. This, however, further slows down the program. See math dot uchicago dot edu/~may/REU2017/REUPapers/Guilhoto.pdf Therefore, the disclosed methods not relying on MCMC can reduce computer memory usage and improve computational speed compared to existing methods applying MCMC techniques such as PyClone.

Further, various implementations of the disclosure can account for CNVs that are not clonal. Namely, they do not assume that all cancer cells are either affected by a CNV or not affected by the CNV. Also they do not assume that all cancer cells carrying a somatic mutation are either affected by CNV are not affected by the CNV.

Because of the above technical properties, the disclosed implementations can achieve more accurate and more valid estimate of CCF and clonality of cancers. They provide more consistent results across various samples. In some implementations, when multiple samples are used, the estimates of CCF and clonality are further improved. Because the implementations do not require MCMC, they can obtain the results 5 orders of magnitude faster than existing methods using MCMC techniques. Also, they require much less computer memory than existing methods using MCMC.

Estimating CCFs and Clonality of Cancer Cells

Overview of Workflow (i) Take Samples

The workflow starts by taking a single sample of a tumor. The tumor might include noncancer cells, which may or may not include a somatic mutation. The tumor sample also includes cancer cells of a first sub-clonal variety, or simply subclone, which may include one or more somatic mutations that are unique to the subclone, and one or more mutations that appear in other subclones or a founding clone. In addition, the sample may include cancer cells of one or more sub-clones besides the first subclone. Each of these additional subclones might have one or more mutations that are unique to its own subclone and or one or more mutations that it shares with one or more other cyclones (e.g., clonal mutations of the founding clone). Certain mutations may be found in all subclone. Such mutations are either clonal mutations or germline mutations. Mutations found only in a subclone are considered sub-clonal. The fraction of cancer cells that include a somatic mutation among all cancer cells (i.e., all subclones) in the tumor is an important property of the tumor.

In some implementations, the sample includes cellular DNA obtained from tissues of a subject. In some implementations, the tumor sample includes cell-free DNA (cfDNA) circulating in bodily fluids and originating from cancer cells.

Note that in order to apply the disclosed methods, it presupposes that there are at least two somatic mutations in a given tumor cell. However, a single sample can include one or more subclone. A single variant by definition means that said variant is clonal and that all other cells in the sample are non-cancerous.

Methods disclosed herein can analyze one or more cancer samples from a test individual. In some implementations, analyzing multiple samples improves the accuracy and validity of the results.

The test samples used for the disclosed processes include DNA originating from tumor cells. They can be various tumor samples, see e.g., tissue and fluid samples. See the sample section for further description of relevant test samples.

(ii) Obtaining Sequence Reads from the Samples

The workflow involves sequencing the test samples to provide a coverage (read count or read abundance) for each locus of multiple loci that harbor somatic mutations. Various sequencing technologies described in the Sequencing Method section may be used. The cancer associated alleles and the wild type alleles for the loci are identified. These loci may be identified using known variant calling techniques to identify variants such as SNPs that are associated with cancers. For example, methods for calling variants may be used as described in Ding, et al. (2012), Nature 481: 506-10. Strelka2 is another example of a variant calling tool that reports variants of interest.

In some implementations, SNP mutations are identified. In other implementations, indel mutations are identified. Using the sequence read counts for cancer variant alleles and reference alleles, one can measure variant allele frequency (VAF) for the cancer variant alleles. However, at this stage it is unknown a priori whether variants come from a clone or a subclone of cancer cells.

(iii) Determining Initial Cancer Cell Fraction (iCCF) from Sequence Reads

For each of the multiple loci that are sequenced and for which VAF is measured, an initial cancer cell fraction (iCCF) is calculated as:

$$iCCF = (VAF*N)/(p*n)$$

where N is the average copy number at the locus, p is a tumor purity of a sample, and n is the copy number of the mutant variant allele.

At this stage, an iCCF is approximated for each of the variant alleles of somatic mutations considered in the analysis. In some implementations, to approximate the cancer cell fraction, certain assumptions are made. In some implementations, it is assumed that the average copy number of mutant allele (n) is 1. The assumption will hold for all somatic variants that do not overlap CNVs, that overlaps a copy number loss of a reference allele (an allele not having a somatic mutation), or that overlaps a copy number gain of the reference allele. This is a reasonably acceptable assumption because copy number changes are expected to be rare relative to small variants.

In some implementations, the tumor purity value p can be determined by empirical methods that directly measure tumor purity. In other implementations, p and/or N can be determined based on the sequence reads using CNV calling tools such as Canvas. See, Roller, et al., (2016), Bioinformatics, 32(15), pp. 2375-2377, which is incorporated by reference in its entirety for all purposes.

The implementations do not require an integer copy number estimate for N, but the normalized coverage estimates that estimate the average copy number of that genomic locus across all cells in the sample. The advantage of using the real value normalized to coverage is that the methods avoid the assumptions of clonality of CNV. With that, as long as the initial assumption above holds, the CCF estimates will be valid for variant overlapping both clonal and sub-clonal CNVs.

In some implementations, when N>1, the iCCF estimates made by the disclosed methods could potentially be larger than one. To avoid such a result, the iCCF estimates are capped at one. Therefore, the iCCF estimates are made using the following formula.

$$CCF = \begin{cases} c \text{ if } c < 1 \\ 1 \text{ if } c > 1 \end{cases}$$

$$c = \frac{VAF \times N}{p}$$

(iv) Cluster Somatic Mutations Based on iCCFs

Clustering is a process by which multiple different somatic mutations are grouped into one or more clusters based on their iCCFs. The iCCFs in clusters are then used to determine final CCFs for mutations. One problem with iCCFs is that they are noisy estimates of the true CCF due to various sources of errors. If iCCFs of a set of variants form a cluster, it is inferred that the set of variants exist in a same subclone or a same set of subclones. With this inference, the true CCFs (as opposed to iCCF) of the set of variants in the cluster should be the same. The average or another central estimate of the iCCFs in the cluster would be a more reliable estimate of the true CCF of any variant in the cluster than the iCCF of the variant. Thus, using clustering, one can gain a better estimation of cancer cell fraction for a variant of interest. In some implementations, the number of subclones giving rise the clusters of iCCFs can also be estimated.

The disclosed implementations use variational Bayesian mixture models for clustering. The methods allow for simultaneous clustering and inference of number of clusters. The disclosed implementations are significantly more efficient than stochastic MCMC techniques used by conventional methods such as PyClone. The disclosed implementations cluster somatic variants based on CCF instead of VAF. This allows the implementations to cluster CNV-overlapping somatic variants. The disclosed implementations also allow clustering both within a single sample, and across multiple samples. The clustering can be done using a variety of different mixture models, including binomial, beta, or Gaussian mixture models. Such probabilistic clustering provide posterior probability estimates of one or more variants belonging to each of the different clusters. These probabilities can be used to calculate an overall CCF for a mutation.

In some imitations, clustering iCCFs can determine a number of subclones in the cancer cells, which is a clinically relevant characteristic of cancers. For example, some cancers having a large number of subclones are more drug resistant or more malignant.

(v) Determine Final CCFs (fCCFs) for Each Mutation

A fCCF is an overall score for a mutations in a sample or a subject. The final CCF for a mutation is calculated from probabilities that the mutation belongs to one or more clusters and the average CCFs in the clusters.

One goal of determining a final CCF is to determine among all the cancer cells in a sample or subject, how prevalent is a particular somatic mutation of interest. For example, a particular somatic mutation is known to be associated with a particular mechanism of cancer formation and/or development. If the somatic mutation has a high fCCF, a cancer therapy targeting the particular mechanism may affect a large portion of the cancer cells, thus providing an effective treatment of the cancer. As such, the cancer therapy should be prescribed or initiated. To the contrary, if the somatic mutation has a low fCCF, the cancer therapy targeting the particular mechanism may not be as effective by itself. As such, the cancer therapy should be altered, terminated, or combined with other therapies.

For example, somatic mutations can lead to creation of neoantigens. Neoantigen load is a marker of response to immune checkpoint inhibitors. It has been shown that Neoantigen level positively correlates with efficacy of anti-PD-1 therapy comprising administering pembrolizumab in non-small cell lung cancer. See See, Rizvi et al., Science, 2015, 348 (6230): 124-128. See, also, McGranahan et al., Science, 2016, 351 (6280): 1463-1469. The cancer therapy such as the ones used in the studies comprises immunotherapy targeting a neoantigen associated with a particular mutation. If the CCF of the mutation is low and the neoantigen sub-clonal, the therapy's immune reaction against the subclonal neoantigen may affect a lower portion of cancer cells and lead to poor treatment efficacy.

(vi) Using CCFs or Subclonal Allele Distributions to Determine Cancer Treatment

Some implementations use variant CCFs and/or subclonal allele distributions to determine antigenic complement of sub-clonal populations and/or treatment options to address all sub-clonal populations. In some implementations, the treatment options can be based upon fCCF of a mutation, the average CCF of subclone, or the number of subclones.

An Example Process for Determining Cancer Cell Fraction

Figure 9:
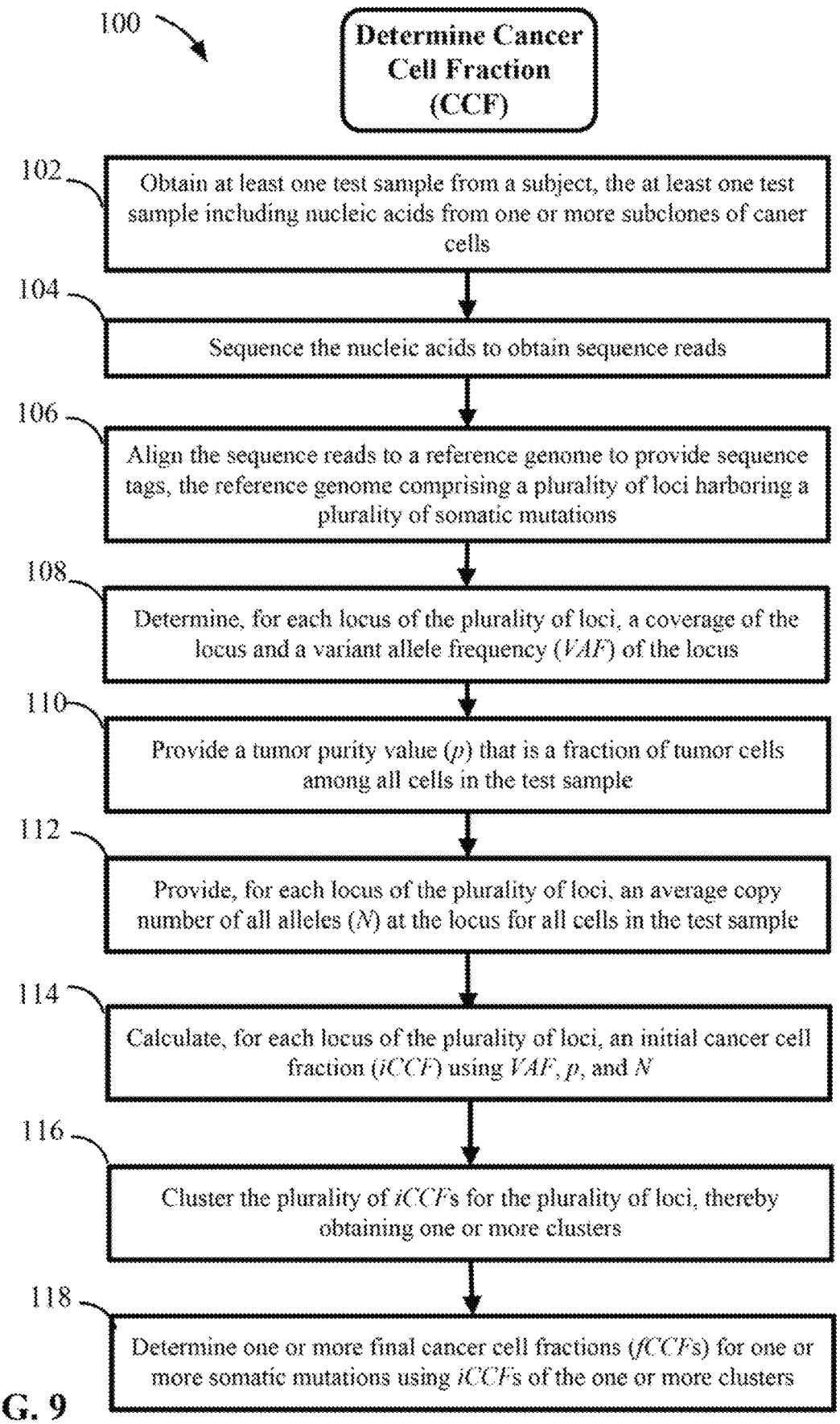
FIG. 9 shows a flow chart illustrating a process for determining cancer cell fraction according to some implementations.
Figure 10:
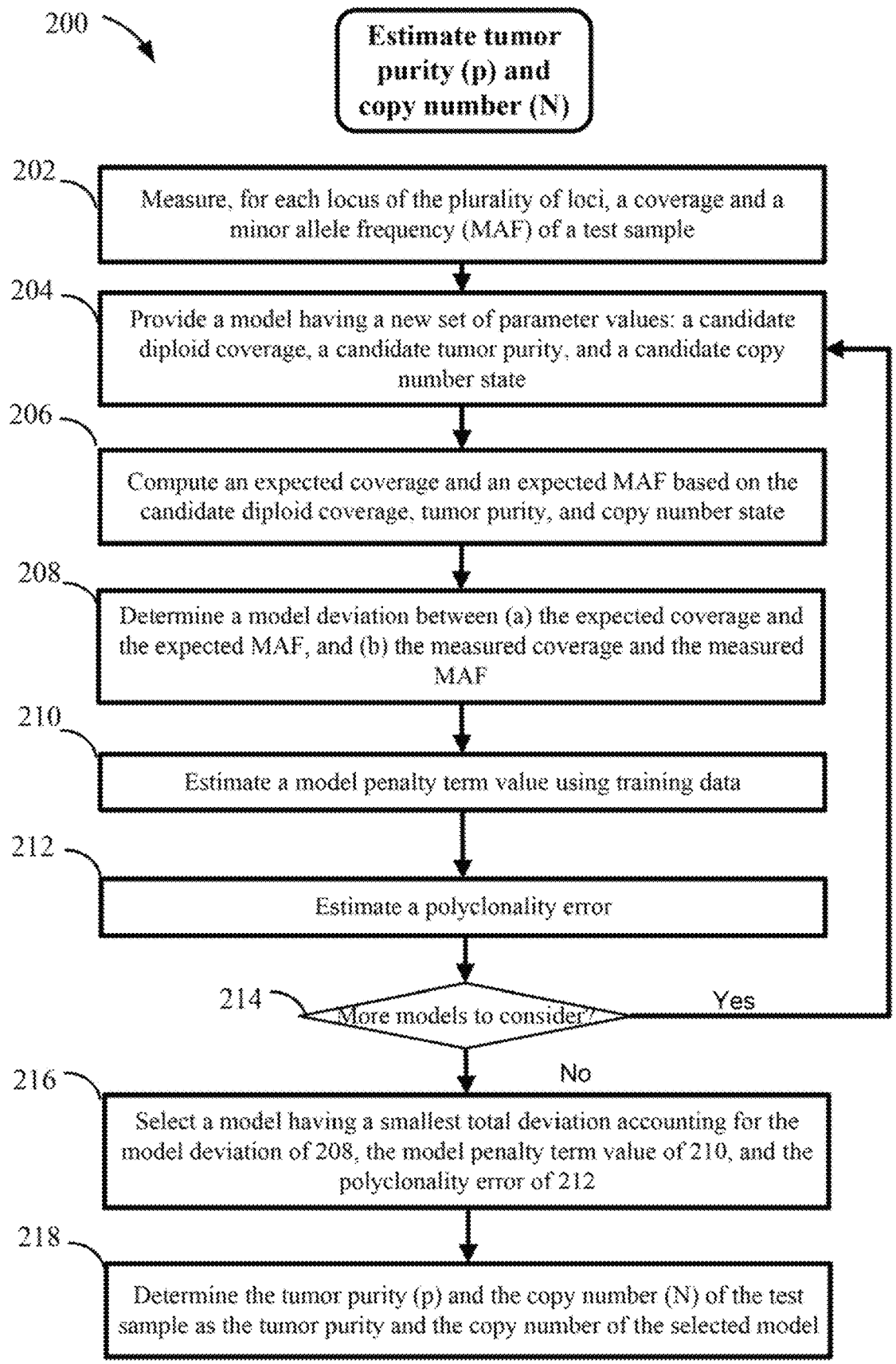
FIG. 10 illustrates a process for estimating tumor purity and copy number using sequence reads.

FIG. 9 shows a flow chart illustrating process 100 for determining cancer cell fraction according to some implementations. Process 100 is implemented using a computer system including one or more processors and system memory. Process 100 involves obtaining at least one test sample from a subject. The at least one test sample includes nucleic acids from one or more sub-clonal of cancer cells. See block 102. In some implementations, the at least one test sample includes two or more test samples. Various samples and sample processing techniques may be used as further described under the Samples section.

In some implementations, the process involves obtaining the at least one test sample from an individual; obtaining cellular DNA or cell free DNA (cfDNA) from the at least one test sample; and sequencing the cellular DNA or cfDNA to produce the sequence reads. See blocks 104. In some implementations, sequencing the nucleic acids involves isolating and/or amplifying the nucleic acids. In some implementations, sequencing the nucleic acids involves whole genome sequencing. In other implementations, sequencing the nucleic acids includes targeted sequencing. Various sequencing methods may be used as described in the Sequencing Methods section.

Process 100 further involves aligning the sequence reads to a reference genome to provide sequence tags. The reference genome includes a plurality of loci harboring a plurality of somatic mutations. Sequence tags are sequence reads that have been aligns to the reference genome and assigned sequence locations. In some implementations, the plurality of somatic mutations includes a mutation selected from the group consisting of a single nucleotide variant (SNV), an indel, or a combination thereof. See block 106.

Process 100 further involves determining, for each locus of the plurality of loci, the coverage of the locus and variant allele frequency of the locus (VAF). A coverage of the locus is a quantity (e.g., counts or normalized counts) of reads aligned to the locus. The VAF is a frequency of a variant allele of the somatic mutation. See block 108.

Process 100 further involves providing tumor purity value (p), which is a fraction of tumor cells among all cells in the test sample. See block 110. Process 100 also involves providing, for each locus of the plurality of loci, and average copy number of all alleles (N) at the locus for all cells in test sample. See block 112. The copy number for different cells may be different. So the average copy number may not be an integer. The average copy number in the process may be determined for a region including multiple loci. In such case, the copy number for the region is used as the copy number for the loci in the region. In some implementations, the tumor purity value (p) is estimated using the sequence reads. In some implementations, the average copy number of alleles (N) is estimated using the sequence reads. Various techniques may be used to estimate tumor purity and copy number using sequence reads.

FIG. 9 illustrates a process for estimating tumor purity and copy number using sequence reads. Process 200 involves measuring, for each locus of the plurality of loci, a coverage and a minor allele frequency (MAF) of the test sample. See block 202.

Process 200 further involves providing a model having a new set of parameter values: a candidate diploid coverage, a candidate tumor purity (p), and a candidate copy number state. The diploid coverage is a read count or abundance measure for diploid cells of a sample. A candidate copy number state describes the alleles and their copy number at a genomic locus. Provided with these parameter values, one can determine an expected coverage and an expected MAF according to the following relations.

Ploidy A: MAF 0
Ploidy AB (normal): MAF 0.5
Ploidy AA (copy-neutral LOH): MAF 0
Ploidy AAB: MAF 0.33333
Ploidy AAA: MAF 0
Ploidy AABB: MAF 0.5
Ploidy AAAB: MAF 0.25
Ploidy AAAA: MAF 0
(etc.)

Process 200 involves computing an expected coverage and an expected MAF based on the candidate diploid coverage, tumor purity, and copy number states according to the relationship above. See block 206.

Process 200 then determines a model deviation between: (a) the expected coverage and the expected MAF obtained in block 206, and (b) the measured coverage and the measured MAF obtained in block 202. See block 208.

Process 200 also involves estimating a penalty term value using training data. See block 210. Further details of the model penalty term are described in Roller, et al., (2016), Bioinformatics, 32(15), pp. 2375-2377, which is incorporated by reference in its entirety for all purposes.

Process 200 also involves estimating a polyclonality error, which relates to how data deviates from clusters corresponding to underlying subclones of cancer cells. See block 212. Further details of the polyclonality error are described in Roller, et al.

Process 200 then evaluates whether more models are to be considered. See decision block 214. If so, the process loops back to block 204 to provide a next model having ano having a new set of parameter values. The process then repeat to determine a model deviation, a model penalty term, and a polyclonality error for the next model. If there are no more models to consider, process 200 proceeds to select a model having the smallest total deviation accounting for the model deviation of 208, the model penalty term value of 210, and the polyclonal analogy error of block 212. See block 216.

After that, process 200 then involves determining a tumor purity (p) and a copy number for the test sample as the tumor purity and copy number of the selected model. See block 218.

Returning to FIG. 1., with the variant allele frequency (VAF), the tumor purity value (p) and the average copy number of alleles (N) provided, process 100 calculates, for each locus of the plurality of loci, an initial cancer cell fraction (iCCF) using VAF, p, and N. See block 114. A cancer cell fraction is a fraction of cancer cells having a somatic mutation at the locus. This operation provides a plurality of iCCFs for the plurality of loci/mutations. In some implementations, the iCCF is calculated based on (VAF*N)/p.

In some patients, the calculation of iCCF includes calculating the iCCF using a copy number of the variant allele (n), as well as VAF, p, and N. In some implementations, the iCCF is calculated based on (VAF*N)/(p*n).

In some implementations, the iCCF is calculated with an assumption that n is 1. In some implementations, the iCCF is calculated using the following formula, which caps iCCF values at 1.

$$CCF = \begin{cases} c \text{ if } c < 1 \\ 1 \text{ if } c > 1 \end{cases}$$

$$c = \frac{VAF \times N}{p}$$

In some implementations, one or more mutations of the plurality of somatic mutations overlap with one or more copy number variations (CNVs). In some implementations, the process does not assume that all cancer cells are either affected by a CNV or not affected by the CNV. In other words, CNV are not necessarily clonal. In such implementations, the parameter N is not always an integer. In some implementations, the process does not assume that all cancer cells carrying somatic mutation are either affected by a CNV or not affected by the CNV. In such implementations, the value of the parameter n may be different for different mutations.

Process 100 further involves clustering the plurality of iCCFs for the plurality of loci, thereby obtaining one or more clusters of iCCs. See block 116. In some implementations, the clustering includes determining one or more posterior probabilities of each mutation belonging to the one or more clusters. In some implementations, the clustering involves using a mixture model to determine the one or more clusters. In some implementations, the mixture model includes a variational Bayesian mixture model. In some implementations, the clustering includes determining a number of subclones of variants that give rise to the plurality of clusters of iCCFs.

In some implementations, the mixture model includes a mixture of two or more probability distributions of variant allele counts of two or more subclones, the variant allele being the allele of the mutant variant. In some implementations, each probability distribution of variant allele counts is a binomial distribution, a beta distribution, a Gaussian distribution, or any combinations thereof. In some implementations, each probability distribution of variant allele counts is a binomial distribution. In some implementations, the variant allele count is calculated based on a sequencing depth and an iCCF. In some implementations, the variant allele count is calculated as: variant allele count=depth× iCCF.

In some implementations, the iCCF of a variant is modeled as a random variable from a beta distribution. In some implementations, the clustering does not use Markov chain Monte Carlo (MCMC) methods. In some implementations, the clustering of block 116 can be implemented using a process depicted in FIG. 11.

Figure 11:
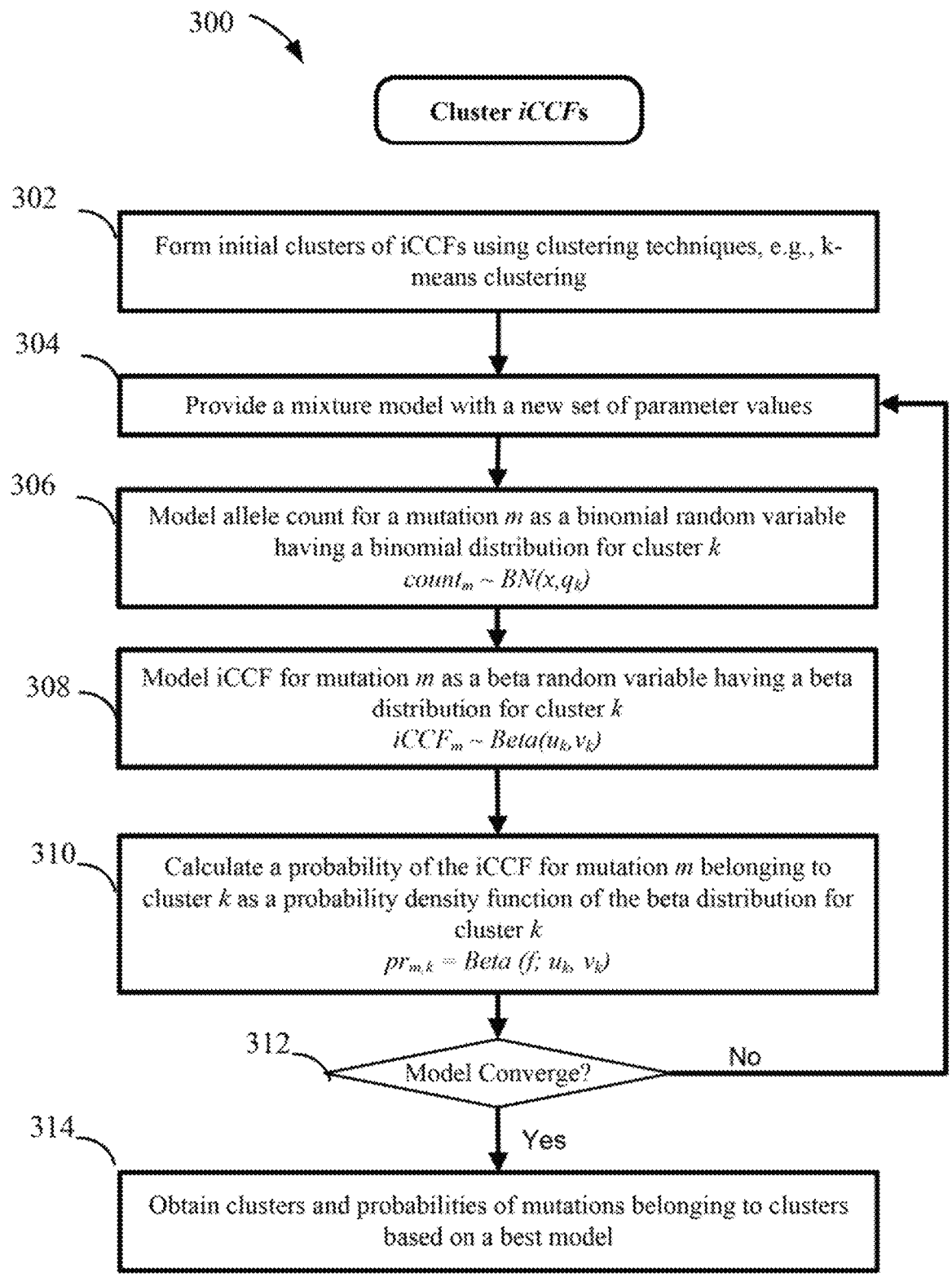
FIG. 11 shows a process for clustering iCCF values.

FIG. 11 shows a process 300 for clustering iCCF values. Process 300 starts by forming initial clusters of iCCFs using clustering techniques, such as K-means clustering. See block 302.

Process 300 then involves providing a mixture model with a new set of parameter values. The mixture model is a variational Bayesian mixture model. See block 304. The mixture model models allele count for mutation m as a binomial random variable from a binomial distribution for cluster k as follows:

$$count_m \sim BN(x, q_k)$$

where BN (,) represents a binomial distribution, x is the total allele count, and $q_k$ is a fraction variant allele among all alleles for cluster k. See block 306.

The mixture model also models iCCF for mutation m as a beta random variable from a beta distribution for cluster k as follows:

$$iCCF_m \sim Beta(u_k, v_k)$$

where Beta represents a beta distribution, and $u_k$ and $v_k$ are shape parameters of the beta distribution for cluster k. See block 308.

Process 300 involves calculating a probability of iCCF for mutation m belonging to cluster k as follows:

$$pr_{m,k} = Beta(f; u_k, v_k) = \frac{\Gamma(u_k + v_k)}{\Gamma(u_k)\Gamma(v_k)} f^{u_k-1}(1-f)^{v_k-1}$$

where $pr_{m,k}$ is a probability that mutation m belongs to cluster k; Beta(;) is a probability density function of a beta distribution for cluster k; f is iCCF for mutation m; and $\Gamma$ is a gamma function. See block 310. In this implementation, the at least one test sample is one sample.

In other implementations, the at least one test sample includes two or more test samples, and the probability of a mutation belonging to a cluster is modeled as:

$$pr_{m,k} = p(f | u_k, v_k) = Beta(f; u_k, v_k) = \prod_{s=1}^{S} Beta(f; u_{ks}, v_{ks})$$

wherein $u_k$ and $v_k$ are the shape parameter vectors whose $s^{th}$ components are $u_{ks}$ and $v_{ks}$, respectively.

In considering a mixture of K (multi-dimensional) beta components, the implementations use a K-dimensional latent binary random variable $z_n$ indicating whether iCCF $f_n$ does ($z_{nk}=1$) or does not ($z_{nk}=0$) belong to component k and satisfying a 1-of-K representation in which $$\sum_{k=1}^{K} z_{nk} = 1.$$

The marginal probability $p(z_{nk}=1)$ that a iCCF belongs to component k is given by its mixing coefficient $\pi_k$, $$p(z_{nk}=1)=\pi_k$$

subject to the probabilistic constraints $$0 \leq \pi_k \leq 1$$

$$\sum_{k=1}^{K} \pi_k = 1$$

Given the 1-of-K representation of $z_n$, this may be written as $$p(z_n | \pi) = \prod_{k=1}^{K} \pi_k^{z_{nk}}$$

Similarly, the conditional distribution $p(f_n|z_n, U, V)$ that an iCCF $f_n$ arises from the mixture may be written $$p(f_n | z_n, U, V) = \prod_{k=1}^{K} Beta(f_n; u_k, v_k)^{z_{nk}}$$

in terms of the shape parameter vectors $u_k$ and $v_k$ of the $k^{th}$ beta component, with aggregate parameters $U \equiv \{u_k\}$ and $V \equiv \{v_k\}$.

See Miller, et al. (2014), PLoS Comput Biol 10(8): e1003665 for further details of the clustering model, which is incorporated by reference in its entirety for all purposes.

Process 300 further involves determining whether the current mixture model converges by comparing expected data and observed data. See block 312. Methods for determining model convergence further described in Miller, et al. (2014). See block 312. If the model does not converge, the process loops back to block 304 to provide a next mixture model with a new set of parameter values and calculate a new set of posterior probabilities of the iCCF. If the model converges, process 300 proceeds to obtain clusters and the probabilities each mutation belonging to the clusters based on the best model. See block 314.

Returning to FIG. 1, in some implementations, the clustering of block 116 allows determination of an averaged iCCF for a cluster or a clone of cells. In some implementations, the clustering allows the determination of a number of sub-clones that give rise to the clusters of iCCFs. In some implementations, these values describe the clonal structure of cancer cells, and they may be used to help design cancer therapy as described herein elsewhere.

After clusters and posterior probabilities are obtained, process 100 proceeds to determine one or more final cancer cell fractions (fCCFs) for one or more somatic mutations using iCCFs of the one or more clusters. See block 118. In some implementations, the each fCCFs are calculated using posterior probabilities of a mutation belonging to multiple clusters and the averages of iCCFs of the clusters. In some implementations, an fCCF for a mutation is calculated as a linear combination of a mean iCCF of somatic mutations in each cluster and a posterior probability of the mutation belonging to each cluster. In some implementations, the fCCF for mutation m is calculated as:

$$fCCF_m = \Sigma_k(\overline{iCCF_k} \times pr_{m,k})$$

wherein $\overline{iCCF_k}$ is the average iCCF of cluster k; and $pr_{m,k}$ is the probability that mutation m belongs to cluster k.

In some implementations, the process can optionally further includes applying a treatment regimen based at least in part on the one or more fCCFs. In some implementations, applying a treatment regimen includes: comparing the one or more fCCFs for the one or more somatic mutations to one or more criteria or threshold values; and prescribing, initiating, and/or altering a treatment regimen based on the comparison. In some implementations, the treatment regimen affects a biological pathway associated with the one or more somatic mutations. In some implementations, the treatment regimen includes an immunotherapy.

Samples

Samples used herein contain nucleic acids that are cell-bound (e.g., cellular DNA) or "cell-free" (e.g., cfDNA). Cellular DNA can be obtained from solid tissues, (e.g., bone, and bone marrow), soft tissues (e.g., organs, muscles, Fat, and skin), or body fluids (e.g., blood, plasma, serum, urine, peritoneal fluid, cerebrospinal fluid, pleural fluid, and amniotic fluid). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, IN, Qiagen, Valencia, CA, Macherey-Nagel, Duren, DE). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the DNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a DNA sequencing library. Non-specific enrichment can be the selective enrichment of one of the two genomes present in a sample that comprises more than one genome. For example, non-specific enrichment can be selective of the cancer genome in a plasma sample, which can be obtained by known methods to increase the relative proportion of cancer to normal DNA in a sample. Alternatively, non-specific enrichment can be the non-selective amplification of both genomes present in the sample. For example, non-specific amplification can be of cancer and normal DNA in a sample comprising a mixture of DNA from the cancer and normal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises at least one biological sample ("test sample"), e.g., as described above. In some embodiments, the nucleic acid(s) to be analyzed is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, trans-cervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

Sequencing Library Preparation

In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Sequencing Methods

As indicated above, the prepared samples (e.g., Sequencing Libraries) are sequenced as part of the procedure for estimating CCF of cancer samples. Any of a number of sequencing technologies can be utilized.

Some sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (Hayward, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA or cellular DNA in a subject being screened for a cancer, and the like, using Illumina's sequencing-by-synthesis and reversible terminator-based sequencing chemistry (e.g. as described in Bentley et al., Nature 6:53-59 [2009]). Template DNA can be genomic DNA, e.g., cellular DNA or cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. Circulating tumor DNA exist in short fragments, with a size distribution peaking at about 150-170 bp. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchor oligos (not to be confused with the anchor/anchored reads in the analysis of repeat expansion). Under limiting-dilution conditions, adapter-modified, single-stranded template DNA is added to the flow cell and immobilized by hybridization to the anchor oligos. Attached DNA fragments are extended and bridge amplified to create an ultra-high density sequencing flow cell with hundreds of millions of clusters, each containing about 1,000 copies of the same template. In one embodiment, the randomly fragmented genomic DNA is amplified using PCR before it is subjected to cluster amplification. Alternatively, an amplification-free (e.g., PCR free) genomic library preparation is used, and the randomly fragmented genomic DNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about tens to a few hundred base pairs are aligned against a reference genome and unique mapping of the short sequence reads to the reference genome are identified using specially developed data analysis pipeline software. After completion of the first read, the templates can be regenerated in situ to enable a second read from the opposite end of the fragments. Thus, either single-end or paired end sequencing of the DNA fragments can be used.

Various embodiments of the disclosure may use sequencing by synthesis that allows paired end sequencing. In some embodiments, the sequencing by synthesis platform by Illumina involves clustering fragments. Clustering is a process in which each fragment molecule is isothermally amplified. In some embodiments, as the example described here, the fragment has two different adaptors attached to the two ends of the fragment, the adaptors allowing the fragment to hybridize with the two different oligos on the surface of a flow cell lane. The fragment further includes or is connected to two index sequences at two ends of the fragment, which index sequences provide labels to identify different samples in multiplex sequencing. In some sequencing platforms, a fragment to be sequenced is also referred to as an insert.

In some implementation, a flow cell for clustering in the Illumina platform is a glass slide with lanes. Each lane is a glass channel coated with a lawn of two types of oligos. Hybridization is enabled by the first of the two types of oligos on the surface. This oligo is complementary to a first adapter on one end of the fragment. A polymerase creates a compliment strand of the hybridized fragment. The double-stranded molecule is denatured, and the original template strand is washed away. The remaining strand, in parallel with many other remaining strands, is clonally amplified through bridge application.

In bridge amplification, a strand folds over, and a second adapter region on a second end of the strand hybridizes with the second type of oligos on the flow cell surface. A polymerase generates a complimentary strand, forming a double-stranded bridge molecule. This double-stranded molecule is denatured resulting in two single-stranded molecules tethered to the flow cell through two different oligos. The process is then repeated over and over, and occurs simultaneously for millions of clusters resulting in clonal amplification of all the fragments. After bridge amplification, the reverse strands are cleaved and washed off, leaving only the forward strands. The 3' ends are blocked to prevent unwanted priming.

After clustering, sequencing starts with extending a first sequencing primer to generate the first read. With each cycle, fluorescently tagged nucleotides compete for addition to the growing chain. Only one is incorporated based on the sequence of the template. After the addition of each nucleotide, the cluster is excited by a light source, and a characteristic fluorescent signal is emitted. The number of cycles determines the length of the read. The emission wavelength and the signal intensity determine the base call. For a given cluster all identical strands are read simultaneously. Hundreds of millions of clusters are sequenced in a massively parallel manner. At the completion of the first read, the read product is washed away.

In the next step of protocols involving two index primers, an index 1 primer is introduced and hybridized to an index 1 region on the template. Index regions provide identification of fragments, which is useful for de-multiplexing samples in a multiplex sequencing process. The index 1 read is generated similar to the first read. After completion of the index 1 read, the read product is washed away and the 3' end of the strand is de-protected. The template strand then folds over and binds to a second oligo on the flow cell. An index 2 sequence is read in the same manner as index 1. Then an index 2 read product is washed off at the completion of the step.

After reading two indices, read 2 initiates by using polymerases to extend the second flow cell oligos, forming a double-stranded bridge. This double-stranded DNA is denatured, and the 3' end is blocked. The original forward strand is cleaved off and washed away, leaving the reverse strand. Read 2 begins with the introduction of a read 2 sequencing primer. As with read 1, the sequencing steps are repeated until the desired length is achieved. The read 2 product is washed away. This entire process generates millions of reads, representing all the fragments. Sequences from pooled sample libraries are separated based on the unique indices introduced during sample preparation. For each sample, reads of similar stretches of base calls are locally clustered. Forward and reversed reads are paired creating contiguous sequences. These contiguous sequences are aligned to the reference genome for variant identification.

The sequencing by synthesis example described above involves paired end reads, which is used in many of the embodiments of the disclosed methods. Paired end sequencing involves two reads from the two ends of a fragment. When a pair of reads are mapped to a reference sequence, the base-pair distance between the two reads can be determined, which distance can then be used to determine the length of the fragments from which the reads were obtained. In some instances, a fragment straddling two bins would have one of its pair-end read aligned to one bin, and another to an adjacent bin. This gets rarer as the bins get longer or the reads get shorter. Various methods may be used to account for the bin-membership of these fragments. For instance, they can be omitted in determining fragment size frequency of a bin; they can be counted for both of the adjacent bins; they can be assigned to the bin that encompasses the larger number of base pairs of the two bins; or they can be assigned to both bins with a weight related to portion of base pairs in each bin.

Paired end reads may use insert of different length (i.e., different fragment size to be sequenced). As the default meaning in this disclosure, paired end reads are used to refer to reads obtained from various insert lengths. In some instances, to distinguish short-insert paired end reads from long-inserts paired end reads, the latter is also referred to as mate pair reads. In some embodiments involving mate pair reads, two biotin junction adaptors first are attached to two ends of a relatively long insert (e.g., several kb). The biotin junction adaptors then link the two ends of the insert to form a circularized molecule. A sub-fragment encompassing the biotin junction adaptors can then be obtained by further fragmenting the circularized molecule. The sub-fragment including the two ends of the original fragment in opposite sequence order can then be sequenced by the same procedure as for short-insert paired end sequencing described above. Further details of mate pair sequencing using an Illumina platform is shown in an online publication at the following URL, which is incorporated by reference by its entirety: resl.lilluminal.lcom/documents/products/technotes/technote_nextera_matepair_data_processing. Additional information about paired end sequencing can be found in U.S. Pat. No. 7,601,499 and US Patent Publication No. 2012/0,053,063, which are incorporated by reference with regard to materials on paired end sequencing methods and apparatuses.

After sequencing of DNA fragments, sequence reads of predetermined length, e.g., 100 bp, are mapped or aligned to a known reference genome. The mapped or aligned reads and their corresponding locations on the reference sequence are also referred to as tags. In one embodiment, the reference genome sequence is the NCBI36/hg18 sequence, which is available on the world wide web at genome dot ucsc dot edu/cgi-bin/
hgGateway?org=Human&db=hg18&hgsid=166260105).
Alternatively, the reference genome sequence is the GRCh37/hg19, which is available on the World Wide Web at genome dot ucsc dot edu/cgi-bin/hgGateway. Other sources of public sequence information include GenBank, dbEST, dbSTS, EMBL (the European Molecular Biology Laboratory), and the DDBJ (the DNA Databank of Japan). A number of computer programs are available for aligning sequences, including but not limited to BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

In one illustrative, but non-limiting, embodiment, the methods described herein comprise obtaining sequence information for the nucleic acids in a test sample, e.g., cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, e.g., cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi), which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, e.g., cfDNA in a test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample, e.g., cfDNA in a test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting, embodiment, the methods described herein comprise obtaining sequence information for the nucleic acids in the test sample, e.g., cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, e.g., cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample using transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like.

Hybridization to the beads can be determined and used to identify the plurality of polynucleotide sequences within the sample.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $1\times10^5$ sequence tags comprising between 75 bp read are obtained from mapping the reads to the reference genome per sample.

The accuracy required for correctly estimating CCFs of cancer samples, is predicated on the variation of the number of sequence tags that map to the reference genome among samples within a sequencing run (inter-run variability), and the variation of the number of sequence tags that map to the reference genome in different sequencing runs (inter-run variability). Other variations can result from using different protocols for the extraction and purification of the nucleic acids, the preparation of the sequencing libraries, and the use of different sequencing platforms.

Apparatus and System for Estimating Cancer Cell Fraction (CCF)

Analysis of the sequencing data and the diagnosis derived therefrom are typically performed using various computer programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), calls such as SNV or aneuploidy calls, CCF estimates, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating CCFs of variants, e.g., variants associated with a cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to estimate CCFs of one or more variants in one or more cancer samples. In one example, the computer product comprises a computer readable medium having a computer executable or compilable logic (e.g., instructions) recorded thereon for enabling a processor to determine CCFs of one or more variants in one or more cancer samples.

The sequence information from the sample under consideration may be mapped to chromosome reference sequences to identify a number of sequence tags for each of any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. The mixture model optimization or computer simulation would be difficult or impossible to perform by human.

The methods disclosed herein can be performed using a system for estimating CCFs of cancer samples. The system comprising: (a) a sequencer for receiving nucleic acids from the test sample providing nucleic acid sequence information from the sample; (b) a processor; and (c) one or more computer-readable storage media having stored thereon instructions for execution on said processor to determine CCFs of one or more variants in one or more cancer samples.

In some embodiments, the methods are instructed by a computer-readable medium having stored thereon computer-readable instructions for carrying out a method for estimating CCFs of cancer samples. Thus one embodiment provides a computer program product comprising one or more computer-readable non-transitory storage media having stored thereon computer-executable instructions that, when executed by one or more processors of a computer system, cause the computer system to implement a method for estimating CCFs of cancer samples. The method includes: (a) receiving sequence reads obtained by sequencing nucleic acids in at least one test sample from an subject, wherein the nucleic acids are from one or more subclones of cancer cells; (b) aligning the sequence reads to a reference genome to provide sequence tags, wherein the reference genome comprises a plurality of loci, each locus of the plurality of loci harboring a somatic mutation of a plurality of somatic mutations; (c) determining, for each locus of the plurality of loci, a coverage of the locus and a variant allele frequency (VAF) of the locus, the VAF being a frequency of a variant allele of the somatic mutation; (d) providing a tumor purity value (p) that is a fraction of tumor cells among all cells in the test sample; (e) providing, for each locus of the plurality of loci, an average copy number of all alleles (N) at the locus for all cells in the test sample; (f) calculating, for each locus of the plurality of loci, an initial cancer cell fraction (iCCF) using VAF, p, and N, wherein a cancer cell fraction is a fraction of cancer cells having the somatic mutation at the locus, thereby obtaining a plurality of iCCFs for the plurality of loci; (g) clustering the plurality of iCCFs for the plurality of loci, thereby obtaining one or more clusters of iCCFs; and (h) determining one or more final cancer cell fractions (fCCFs) for one or more somatic mutations of the plurality of somatic mutations using iCCFs of the one or more clusters.

In some embodiments, the instructions may further include automatically recording information pertinent to the method in a patient medical record for a human subject providing the test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the test sample was taken. This may involve performing one or more additional tests or analyses on additional samples taken from the subject.

Disclosed methods can also be performed using a computer processing system which is adapted or configured to perform a method for estimating CCFs of cancer samples. One embodiment provides a computer processing system, which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus, which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Allele counts—Counts or numbers of tags for each allele and regions of a reference genome or other reference sequences Determined CCF values, cancer cell clonality, or number of cancer cell subclones Diagnoses (clinical condition associated with the calls)
Recommendations for further tests derived from the calls and/or diagnoses
Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce calls. At this remote location, as an example, the reads are aligned to a reference sequence to produce tags, which are counted and assigned to chromosomes or segments of interest. Also at the remote location, the doses are used to generate calls.

Among the processing operations that may be employed at distinct locations are the following:
Sample collection
Sample processing preliminary to sequencing
Sequencing
Analyzing sequence data and quantifying test samples
Diagnosis
Reporting a diagnosis and/or a call to patient or health care provider
Developing a plan for further treatment, testing, and/or monitoring
Executing the plan
Counseling Any one or more of these operations may be automated as described elsewhere herein. Typically, the sequencing and the analyzing of sequence data and estimating CCFs will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of DNA analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of DNA analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of a DNA analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and estimating CCFs of cancer samples. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 12:
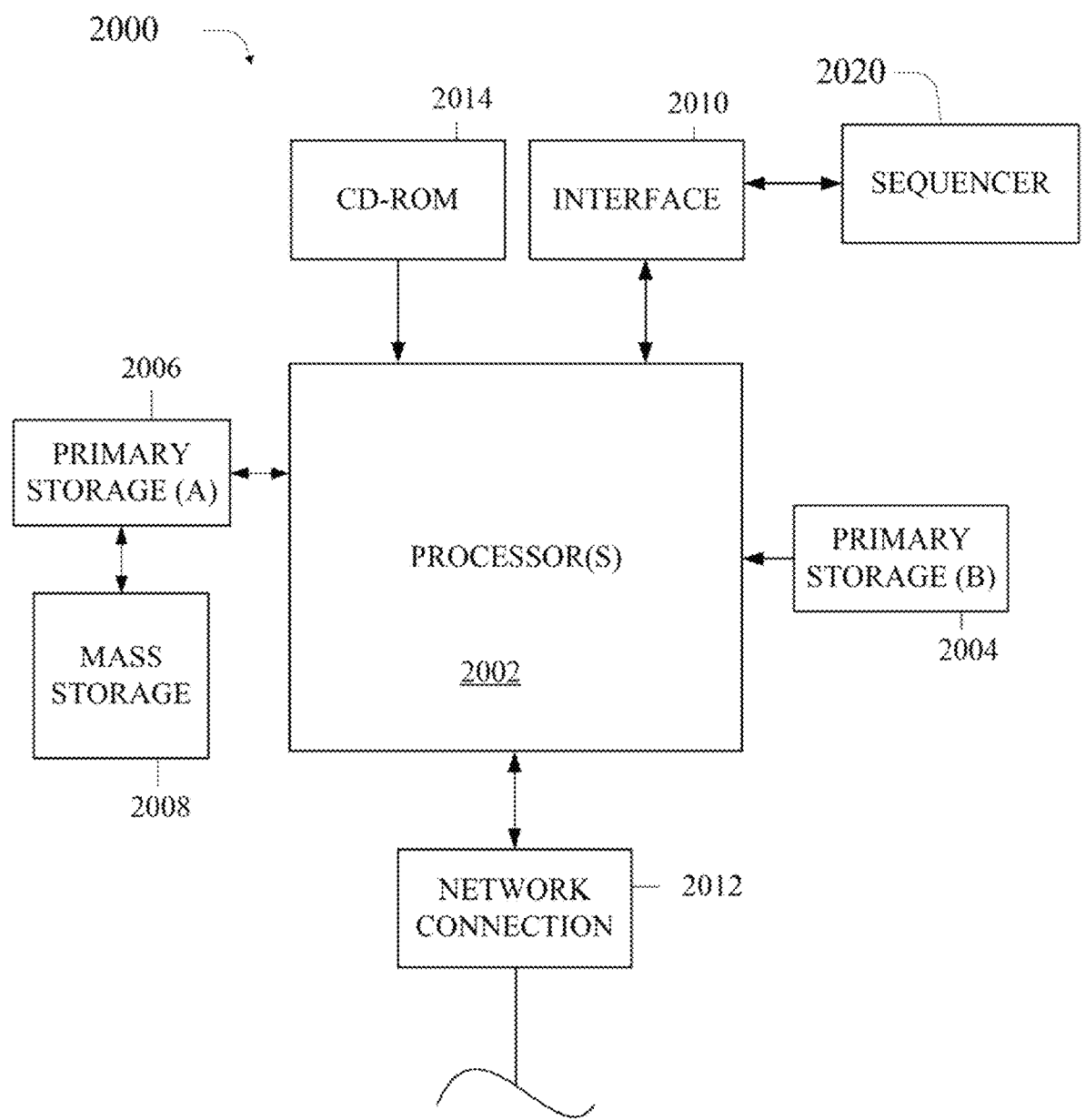
FIG. 12 shows block diagram of a typical computer system that can serve as a computational apparatus according to certain embodiments.

FIG. 12 illustrates, in simple block format, a typical computer system that, when appropriately configured or designed, can serve as a computational apparatus according to certain embodiments. The computer system 2000 includes any number of processors 2002 (also referred to as central processing units, or CPUs) that are coupled to storage devices including primary storage 2006 (typically a random access memory, or RAM), primary storage 2004 (typically a read only memory, or ROM). CPU 2002 may be of various types including microcontrollers and microprocessors such as programmable devices (e.g., CPLDs and FPGAs) and non-programmable devices such as gate array ASICs or general-purpose microprocessors. In the depicted embodiment, primary storage 2004 acts to transfer data and instructions uni-directionally to the CPU and primary storage 2006 is used typically to transfer data and instructions in a bi-directional manner. Both of these primary storage devices may include any suitable computer-readable media such as those described above. A mass storage device 2008 is also coupled bi-directionally to primary storage 2006 and provides additional data storage capacity and may include any of the computer-readable media described above. Mass storage device 2008 may be used to store programs, data and the like and is typically a secondary storage medium such as a hard disk. Frequently, such programs, data and the like are temporarily copied to primary memory 2006 for execution on CPU 2002. It will be appreciated that the information retained within the mass storage device 2008, may, in appropriate cases, be incorporated in standard fashion as part of primary storage 2004. A specific mass storage device such as a CD-ROM 2014 may also pass data uni-directionally to the CPU or primary storage.

CPU 2002 is also coupled to an interface 2010 that connects to one or more input/output devices such as such as a nucleic acid sequencer (2020), video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, C P U 2002 optionally may be coupled to an external device such as a database or a computer or telecommunications network using an external connection as shown generally at 2012. With such a connection, it is contemplated that the CPU might receive information from the network, or might output information to the network in the course of performing the method steps described herein. In some implementations, a nucleic acid sequencer (2020) may be communicatively linked to the CPU 2002 via the network connection 2012 instead of or in addition to via the interface 2010.

In one embodiment, a system such as computer system 2000 is used as a data import, data correlation, and querying system capable of performing some or all of the tasks described herein. Information and programs, including data files can be provided via a network connection 2012 for access or downloading by a researcher. Alternatively, such information, programs and files can be provided to the researcher on a storage device.

In a specific embodiment, the computer system 2000 is directly coupled to a data acquisition system such as a microarray, high-throughput screening system, or a nucleic acid sequencer (2020) that captures data from samples. Data from such systems are provided via interface 2010 for analysis by system 2000. Alternatively, the data processed by system 2000 are provided from a data storage source such as a database or other repository of relevant data. Once in apparatus 2000, a memory device such as primary storage 2006 or mass storage 2008 buffers or stores, at least temporarily, relevant data. The memory may also store various routines and/or programs for importing, analyzing and presenting the data, including sequence reads, UMIs, codes for determining sequence reads, collapsing sequence reads and correcting errors in reads, etc.

In certain embodiments, the computers used herein may include a user terminal, which may be any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms.

In certain embodiments, the computers used herein may also include a server system in communication with a user terminal, which server system may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Figure 13:
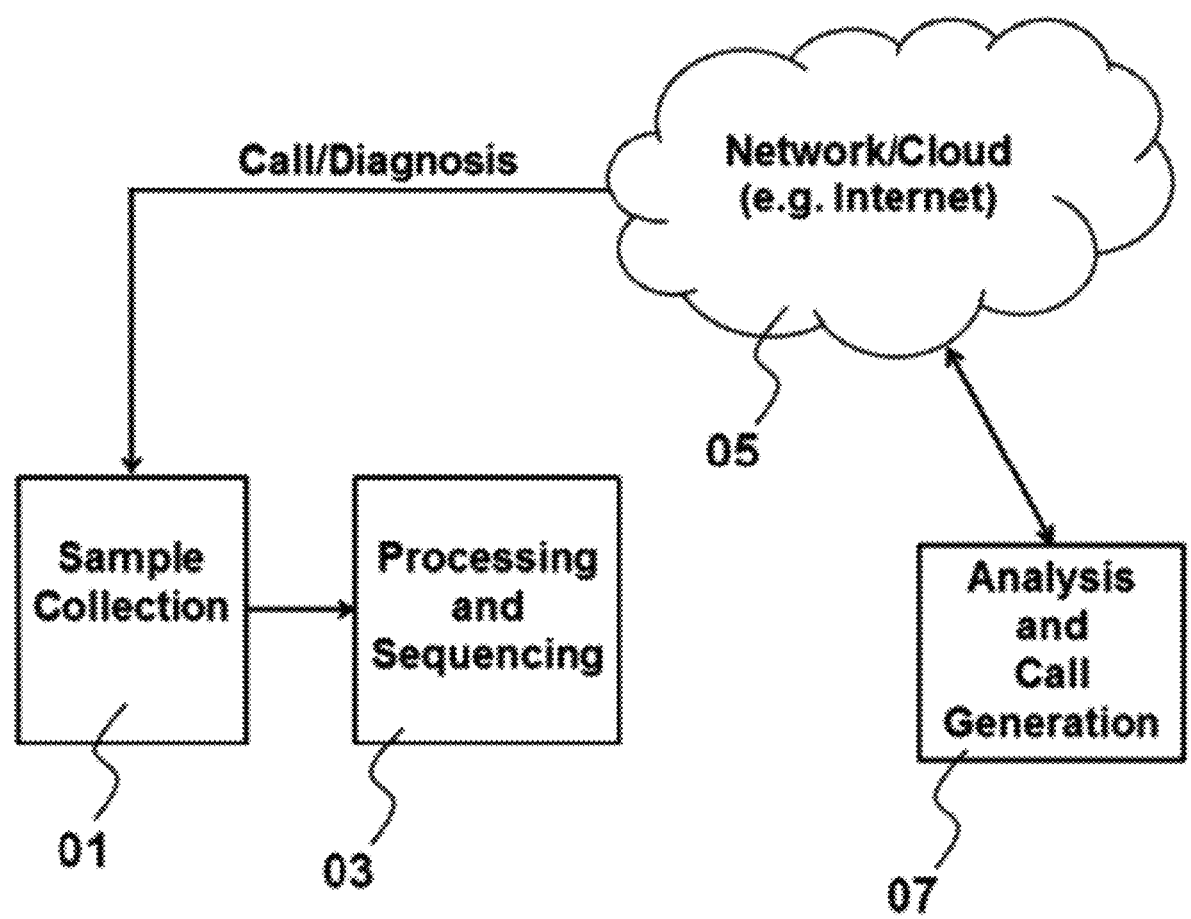
FIG. 13 shows one implementation of a dispersed system for producing a call or diagnosis from a test sample.

FIG. 13 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 13.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 5. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 14:
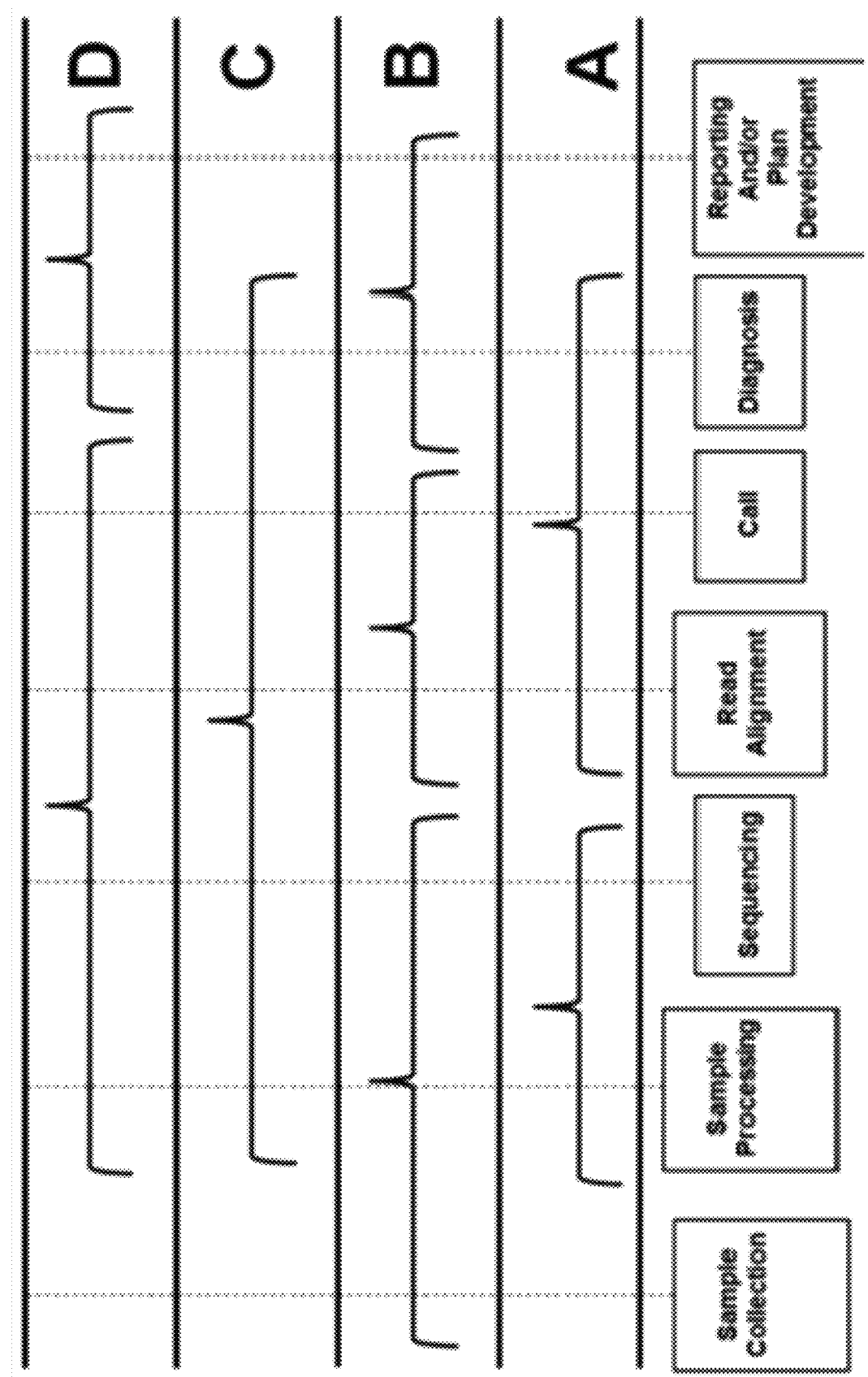
FIG. 14 shows options for performing various operations of some implementations at distinct locations.

FIG. 14 elaborates on the options for performing various operations at distinct locations. In the most granular sense depicted in FIG. 14, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 14 identified by reference character A. In another implementation, which is identified by character B in FIG. 14, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 14, sample collection is performed at a first location, sample processing, sequencing, read alignment, calling, and diagnosis are all performed together at a second location, and reporting and/or plan development are performed at a third location. Finally, in the implementation labeled D in FIG. 14, sample collection is performed at a first location, sample processing, sequencing, read alignment, and calling are all performed at a second location, and diagnosis and reporting and/or plan management are performed at a third location.

One embodiment provides a system for analyzing cell-free DNA (cfDNA) for simple nucleotide variants associated with tumors, the system including a sequencer for receiving a nucleic acid sample and providing nucleic acid sequence information from the nucleic acid sample; a processor; and a machine readable storage medium comprising instructions for execution on said processor, the instructions includes: (a) receive genomic sequence data obtained by sequencing nucleic acids in at least one test sample from a subject, wherein the nucleic acids are from one or more subclones of cancer cells; (b) determine a plurality of somatic mutation variants in the genomic sequence data; (c) calculate, for each somatic mutation variant, an initial cancer cell fraction (iCCF) using a VAF, wherein a cancer cell fraction is a fraction of cancer cells having the somatic mutation variant among all cancer cells, and wherein the VAF is an allele frequency of the somatic mutation variant, thereby obtaining a plurality of iCCFs for the plurality of somatic mutation variants; (d) cluster the plurality of iCCFs for the plurality of loci, thereby obtaining one or more clusters of iCCFs, each cluster corresponding to variants present in a same subclone of the one or more tumor subclones; and (e) determine one or more final cancer cell fractions (fCCFs) for one or more somatic mutations of the plurality of somatic mutations using iCCFs of the one or more clusters.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

EXPERIMENTAL

Example 1: Simulation Data

Figure 15:
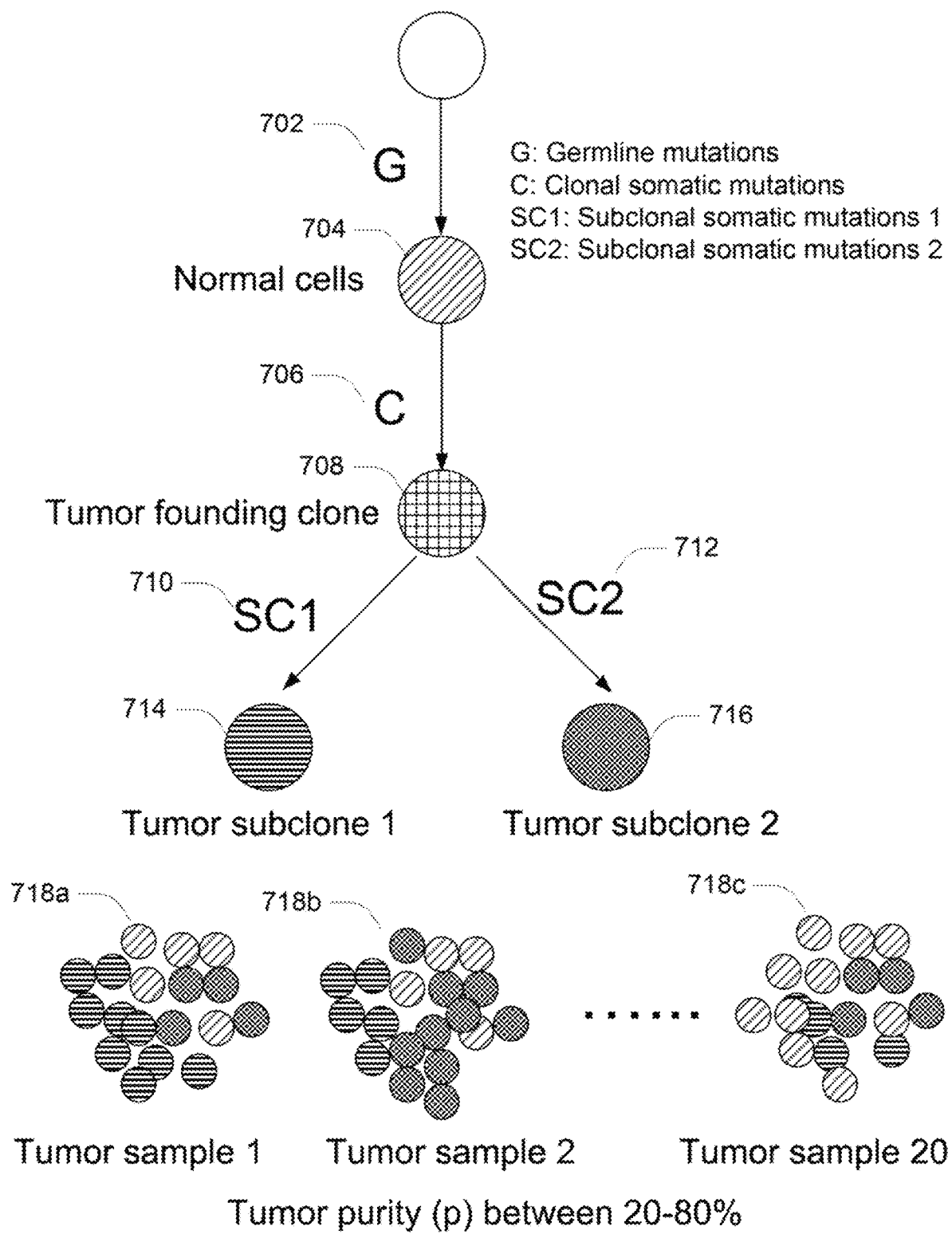
FIG. 15 illustrates a method of generating simulation data of 20 tumor samples having different compositions from normal cells and two tumor subclones.

This example uses simulation data to compare a method according to some implementations and referred to as ClonScore and a prior method PyClone. FIG. 15 illustrates the method used in the example for generating simulation data of 20 tumor samples having different compositions from normal cells and two tumor subclones. The normal cell population is illustrated as circle 704. The tumor founding clone is illustrated as circle 708. The two tumor subclones are illustrated as circles 714 and 716. The normal cells include germline mutations "G" (702). The tumor founding clone (708) includes clonal somatic mutations "C" (706). The tumor subclone 1 (714) includes sub-clonal somatic mutations 1 "SC1" (710). The tumor subclone 2 (716) includes sub-clonal somatic mutations 2 "SC2" (712). The two tumor subclones also include the clonal somatic mutations "C" (706). Tumor samples 718a, 718b, and 718c have different cell and mutation compositions. The tumor purity (p) of the samples ranges 20-80%. Two simulated whole exome sequence (WES) data sets were generated for this example. Each data set includes 20 samples with varying portions of two different tumor subclones and normal cells.

Targeted regions in the data set were defined as those specified in a TruSeq exome assay (covers about ~45 Mb), with 150 bps padding up and downstream of each target. Germline SNPs (90,000) and INDELs (12,000) were randomly chosen from dbsnp, and included in all tumor subclones and normal cells. Regions affected by germline CNVs were randomly chosen from DGV, and variations in copy number over such regions were chosen randomly and ranged from loss of both copies to duplication of both alleles. These germline mutations are illustrated as the "G" wave mutations (702). Two different tumor subclones "SC1" (710) and "SC2" (712) were also created. A set of 500 somatic SNVs, 200 INDELs, and 75 CNVs (5 LOH, 30 gains of 5 copies of one allele, 20 single copy deletions, and 20 gains of 8 copies of one allele) that overlapped at least one targeted region were randomly chosen from COSMIC and included in both tumor subclones (clonal variants). They are illustrated as the "C" wave mutations (706). A different set of 500 somatic SNVs, 200 INDELs, and 75 CNVs (same distribution of copy number as above) from COSMIC, was included in subclone "SC1" (710), and a different set of mutations of the same size was were included in subclone "SC2" (712). Note that when CNVs overlapped SNVs, they had an equal chance of affecting the allele carrying the mutation or the other allele. Therefore, many such CNVs do lead to increases in the copy number of the mutated allele (situation where ClonScore is expected to have difficulties). Reads from each subclone and from normal cells were simulated, and mixed together in different proportions in order to create the 20 different tumor samples.

After processing this dataset using the Enrichment and TumorNormal workflows, we estimated the fCCF for each somatic SNV that was called. The fCCF estimation was done using both PyClone and ClonScore in the single sample mode. For PyClone, Canvas' allelic copy number calls were used for any somatic SNV that overlapped a CNV call. For ClonScore, Canvas' normalized coverage was used as estimates of N whenever the normalized coverage was outside the [1.9,2.1] interval, otherwise N was assumed to be 2. Tumor purity estimates made by Canvas were used both in PyClone and in ClonScore estimates.

Figure 16:
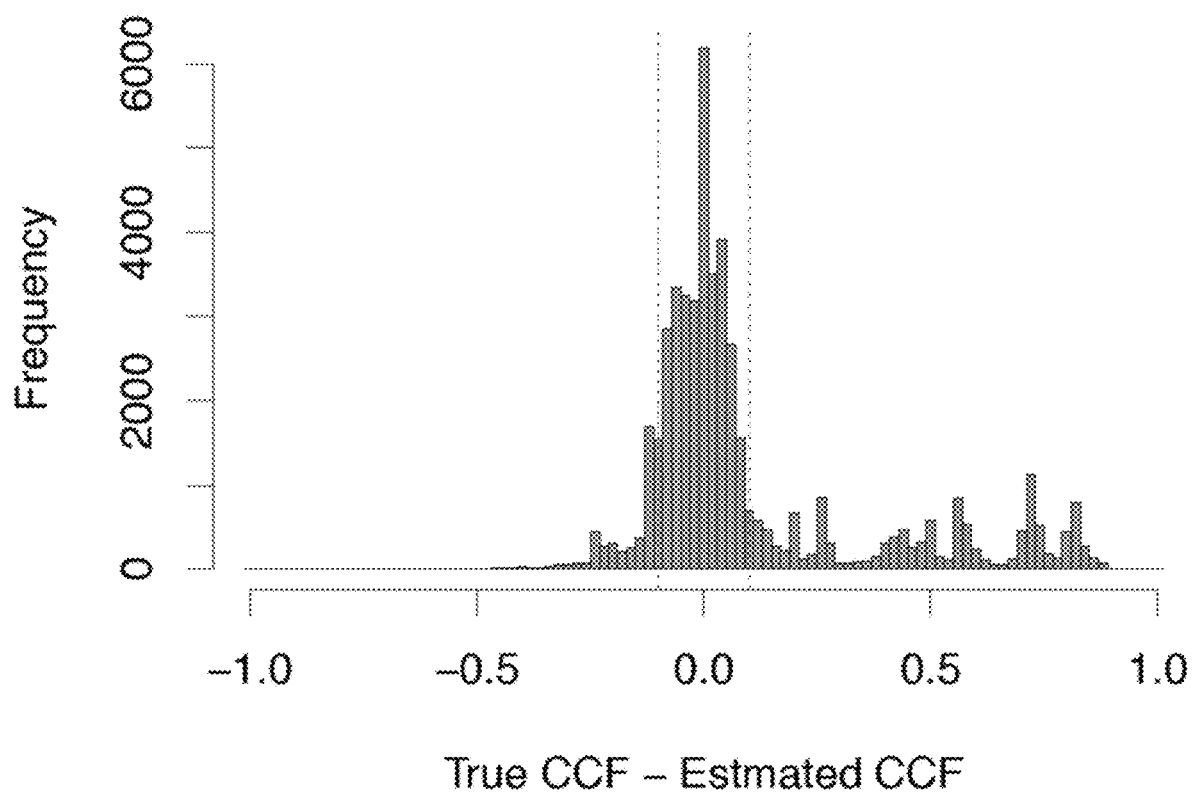
FIG. 16 shows the estimated CCFs deviation from true CCFs for PyClone.
Figure 17:
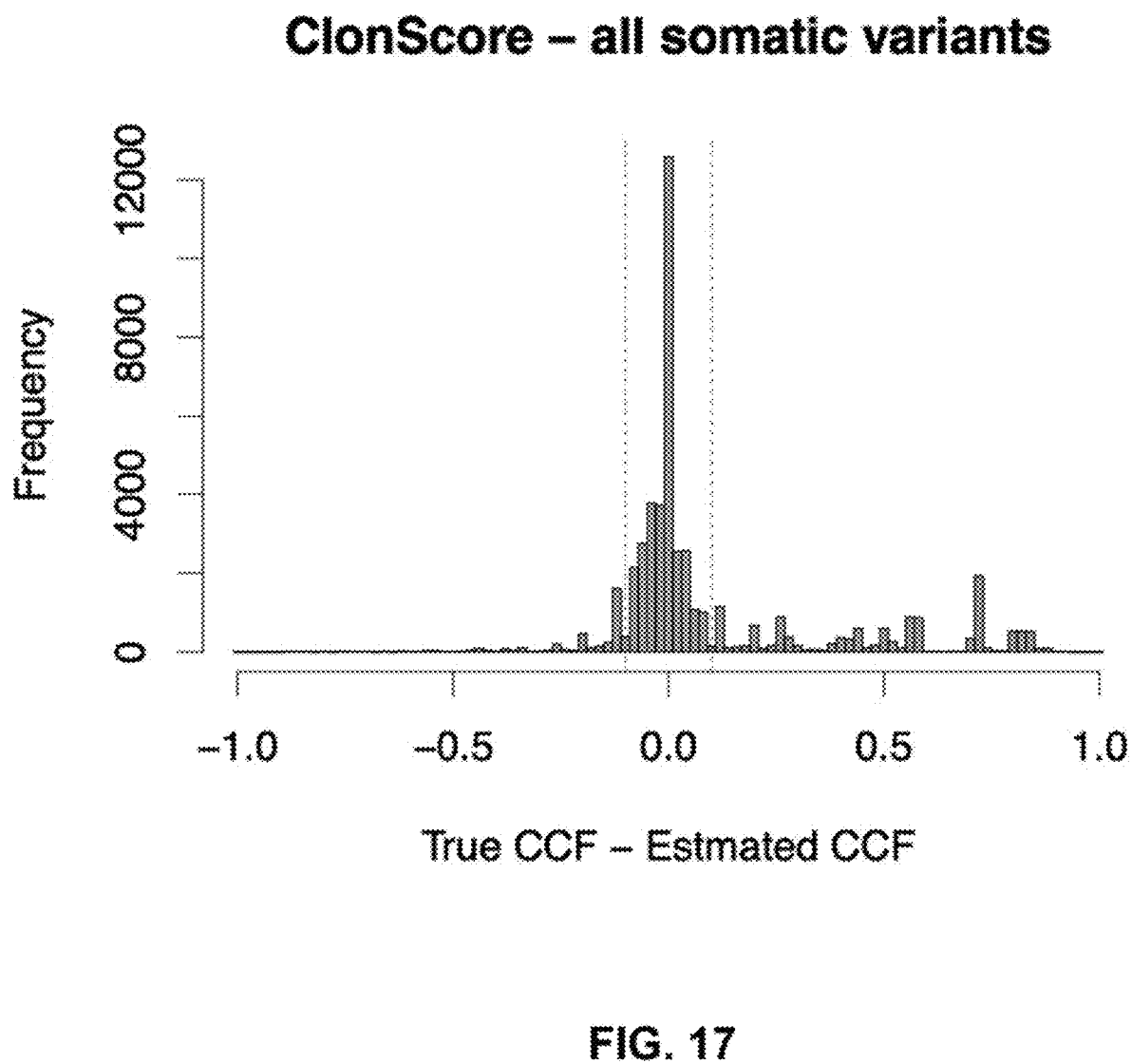
FIG. 17 shows the estimated CCFs deviation from true CCFs for ClonScore.

FIG. 16 shows the estimated CCFs deviation from true CCFs for PyClone. FIG. 17 shows the results for ClonScore. These results include estimates for all SNVs in all of the 40 samples across the 2 simulated WES datasets. Note that ClonScore estimates are closer to the true CCF than PyClone's estimates. Further, while PyClone took around 7 hours to run on each tumor WES experiment, ClonScore took only seconds.

Example 1: Real Cancer Data

The most commonly used method for studying intra-tumor heterogeneity is currently multi-site sequencing of tumor samples. The accuracy of clonality estimating tools when analyzing multiple samples of the same tumor simultaneously is increased, due to the more confident clustering of somatic mutations that can be achieved. In a recent study by Hao et al., multi-site WES was performed on 11 esophageal squamous cell carcinomas. Each of the 11 tumors had 4 spatially separated samples as well as a matched normal sample profiled with WES.

Figure 18:
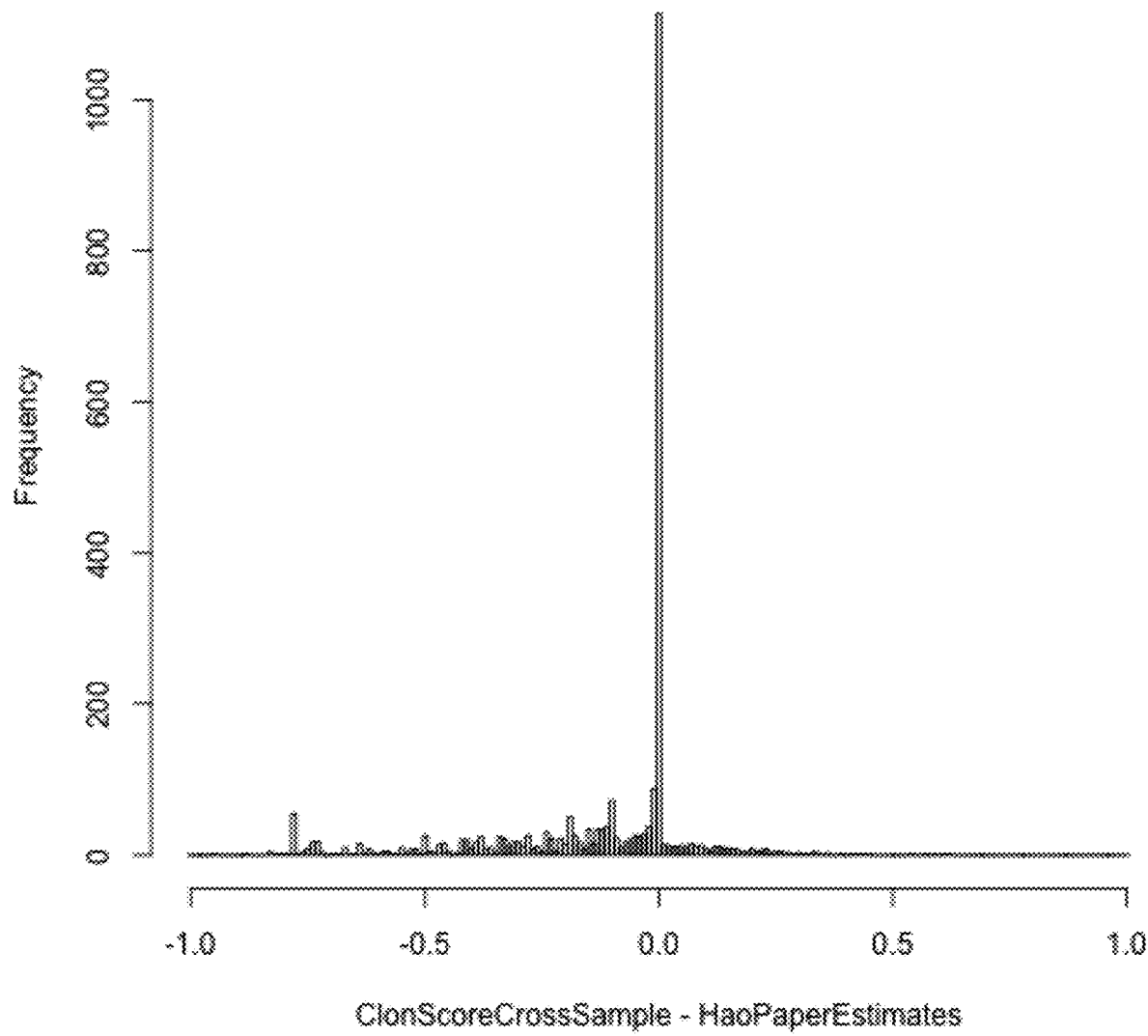
FIG. 18 shows the difference of CCFs between ClonScore and Hao et al. for a multi-sample analysis.
Figure 19:
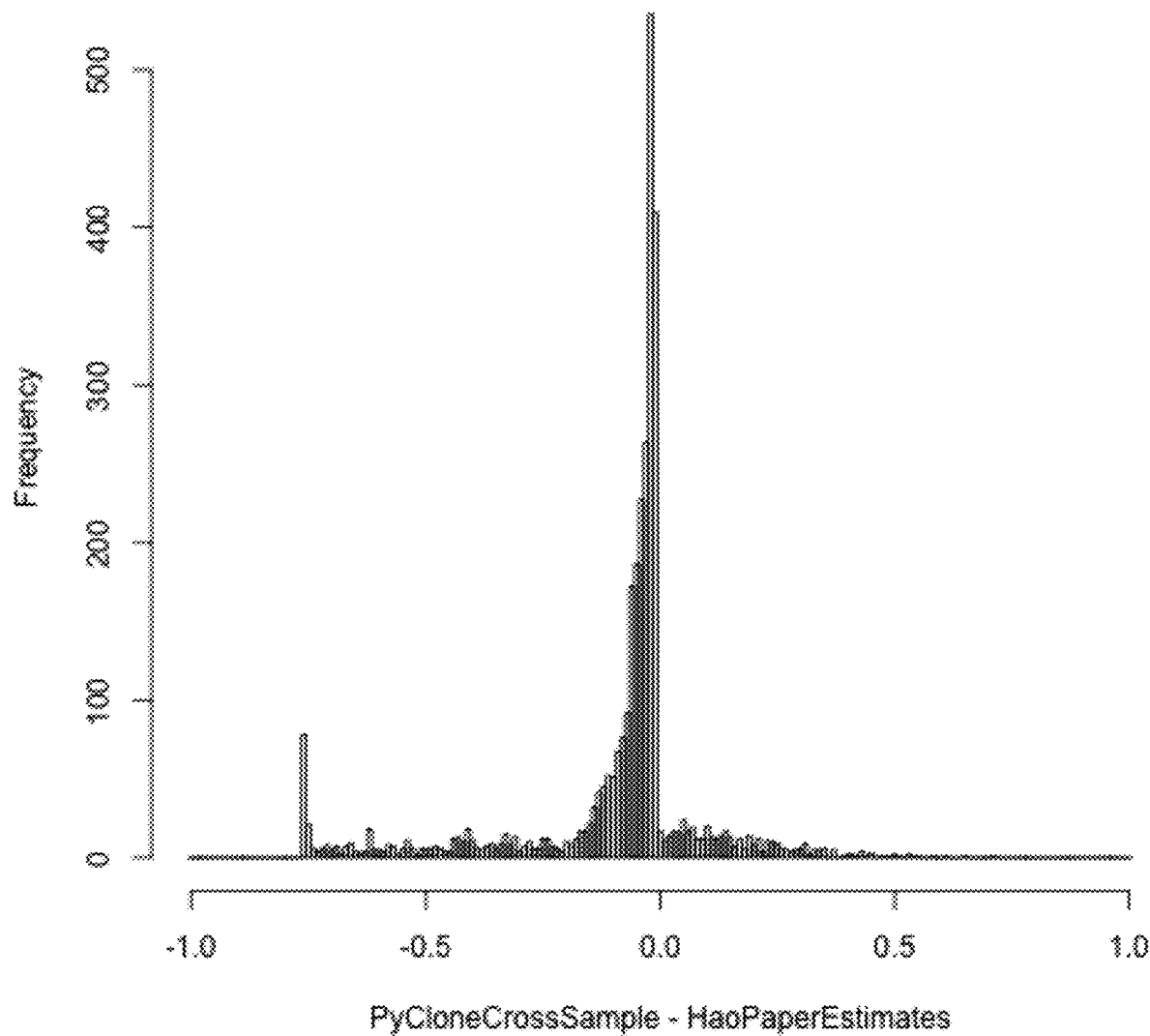
FIG. 19 shows the difference of CCFs between PyClone and Hao et al. for a multi-sample analysis.

We downloaded that dataset and processed it with Enrichment+TumorNormal workflows. PyClone and ClonScore were then applied to that dataset both in single sample mode, as well as by analyzing all four samples of each tumor simultaneously. We first compared the results of multi-sample ClonScore, multi-sample PyClone, and the published CCF estimates. FIG. 18 shows the difference of CCFs between ClonScore and Hao et al. FIG. 19 shows the difference of CCFs between PyClone and Hao et al. The figures show that the results of all multi-sample estimates were relatively consistent, but PyClone's estimates deviate further from those of the other two methods.

Figure 20:
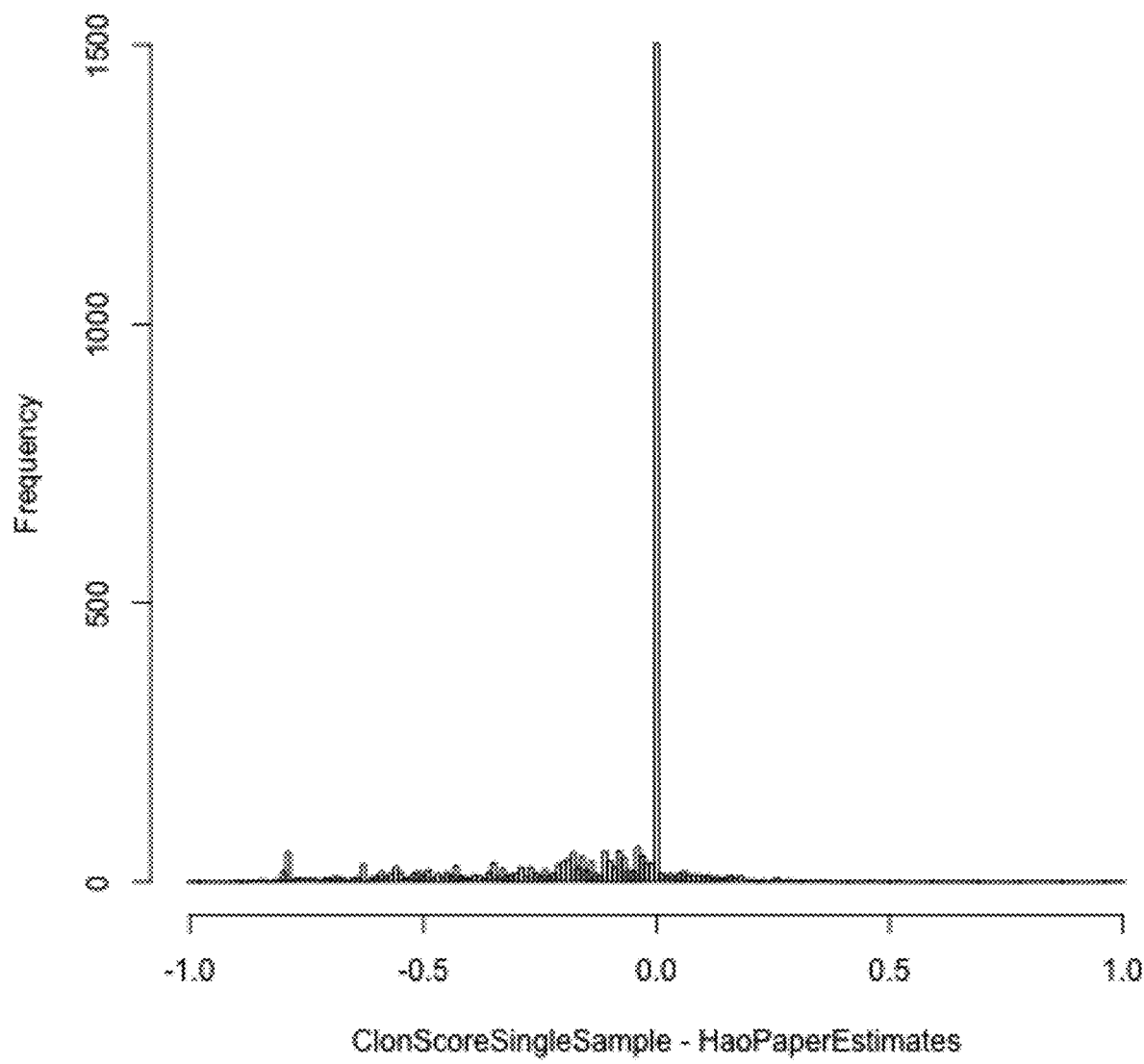
FIGS. 20-22 show estimates of single sample analysis of ClonScore relative to estimates of multi-sample analyses of methods by Hao (FIG. 20), PyClone (FIG. 21), and ClonScore (FIG. 22).
Figure 21:
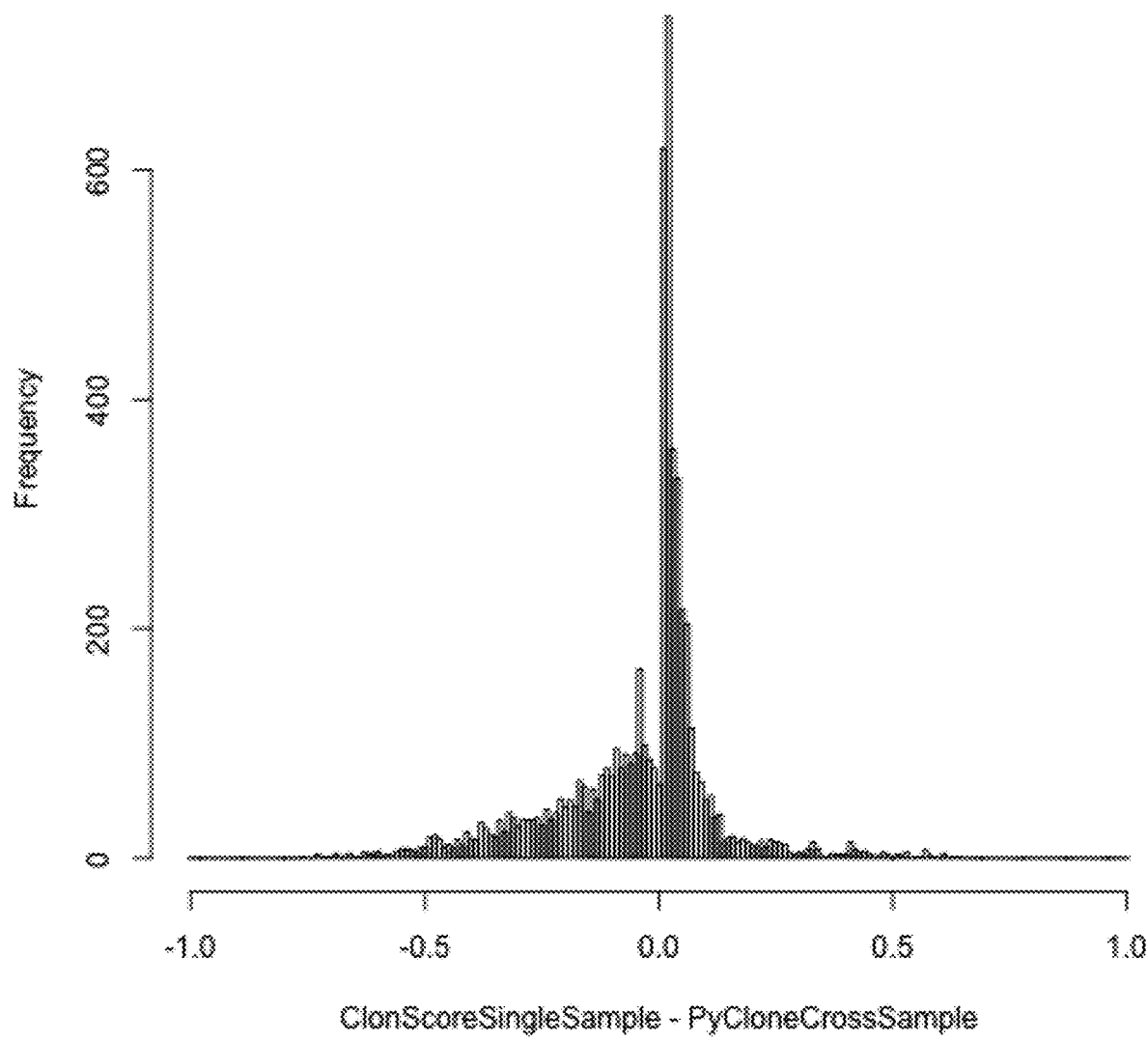
Figure 22:
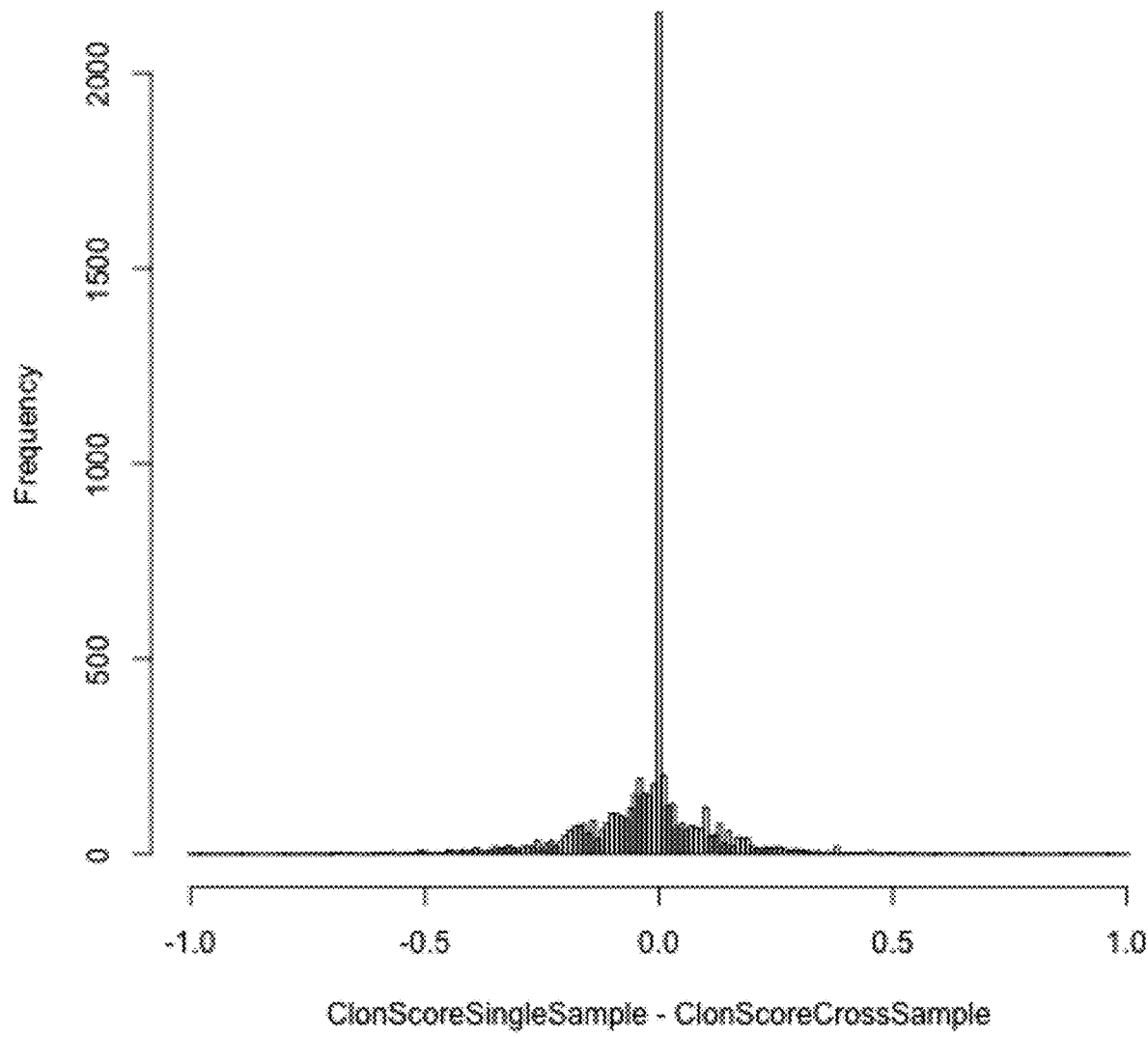
Figure 23:
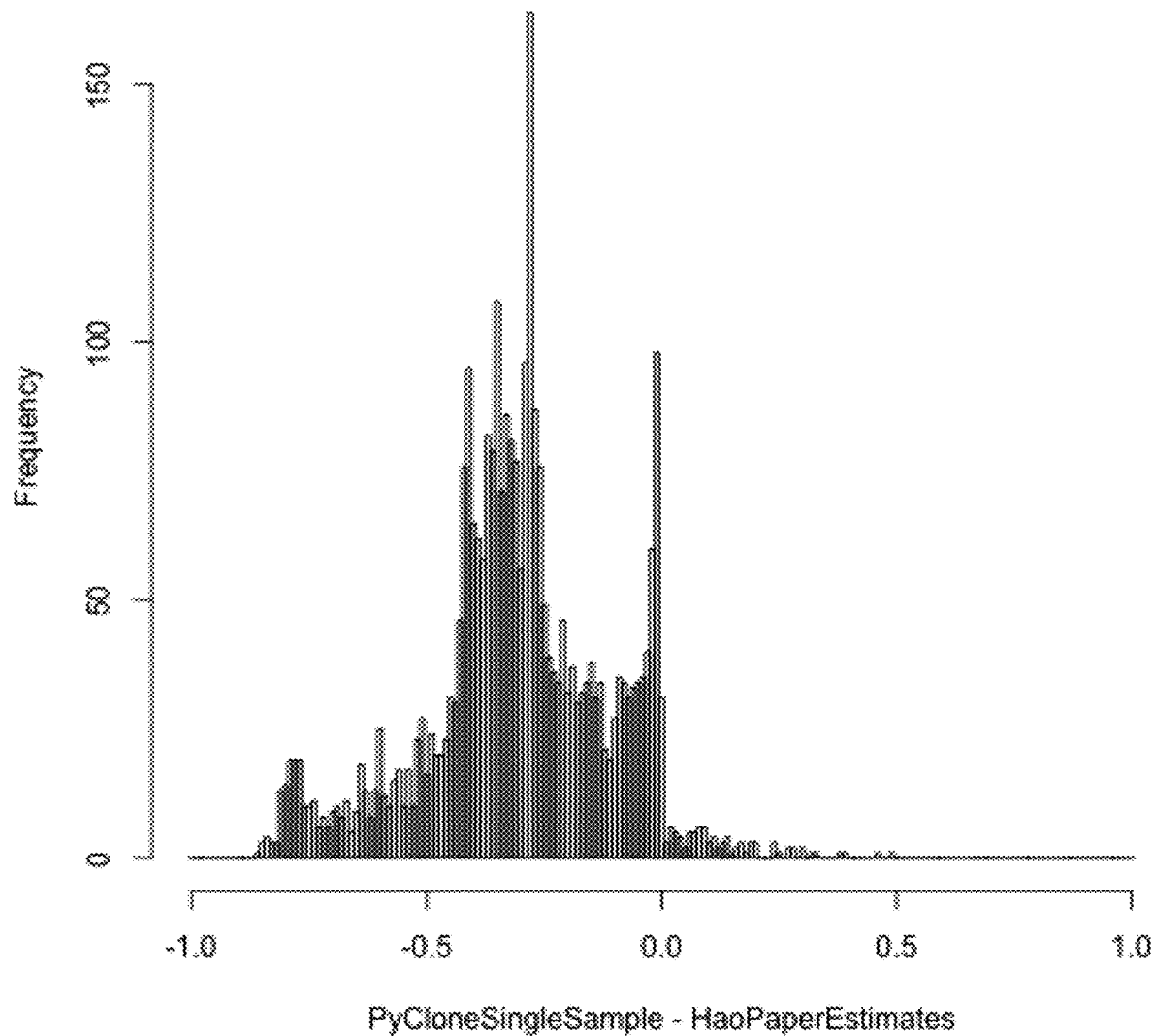
FIGS. 23-25 show estimates of single sample analysis of PyClone relative to estimates of multi-sample analyses of methods by Hao (FIG. 23), PyClone (FIG. 24), and ClonScore (FIG. 25).
Figure 24:
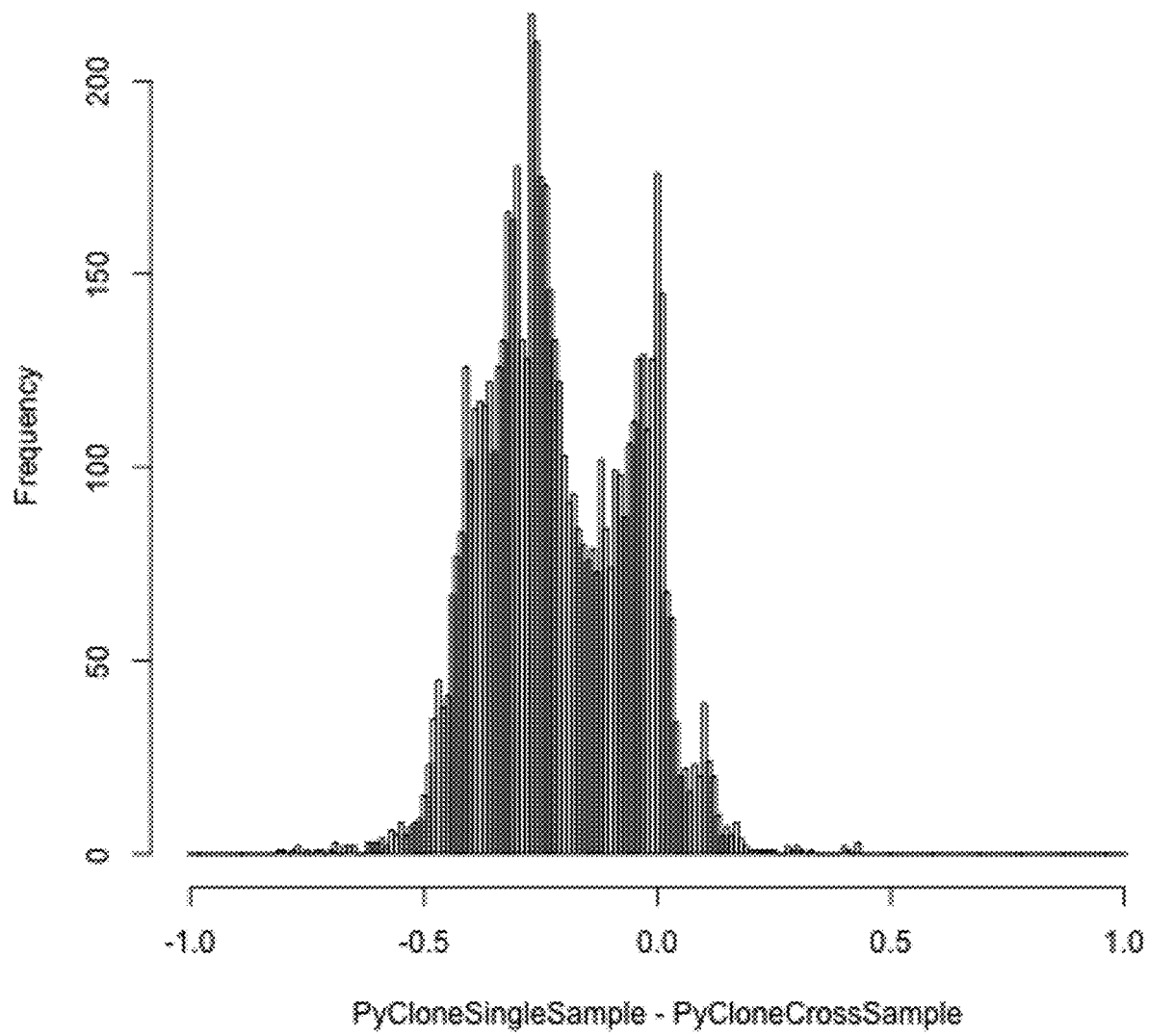
Figure 25:
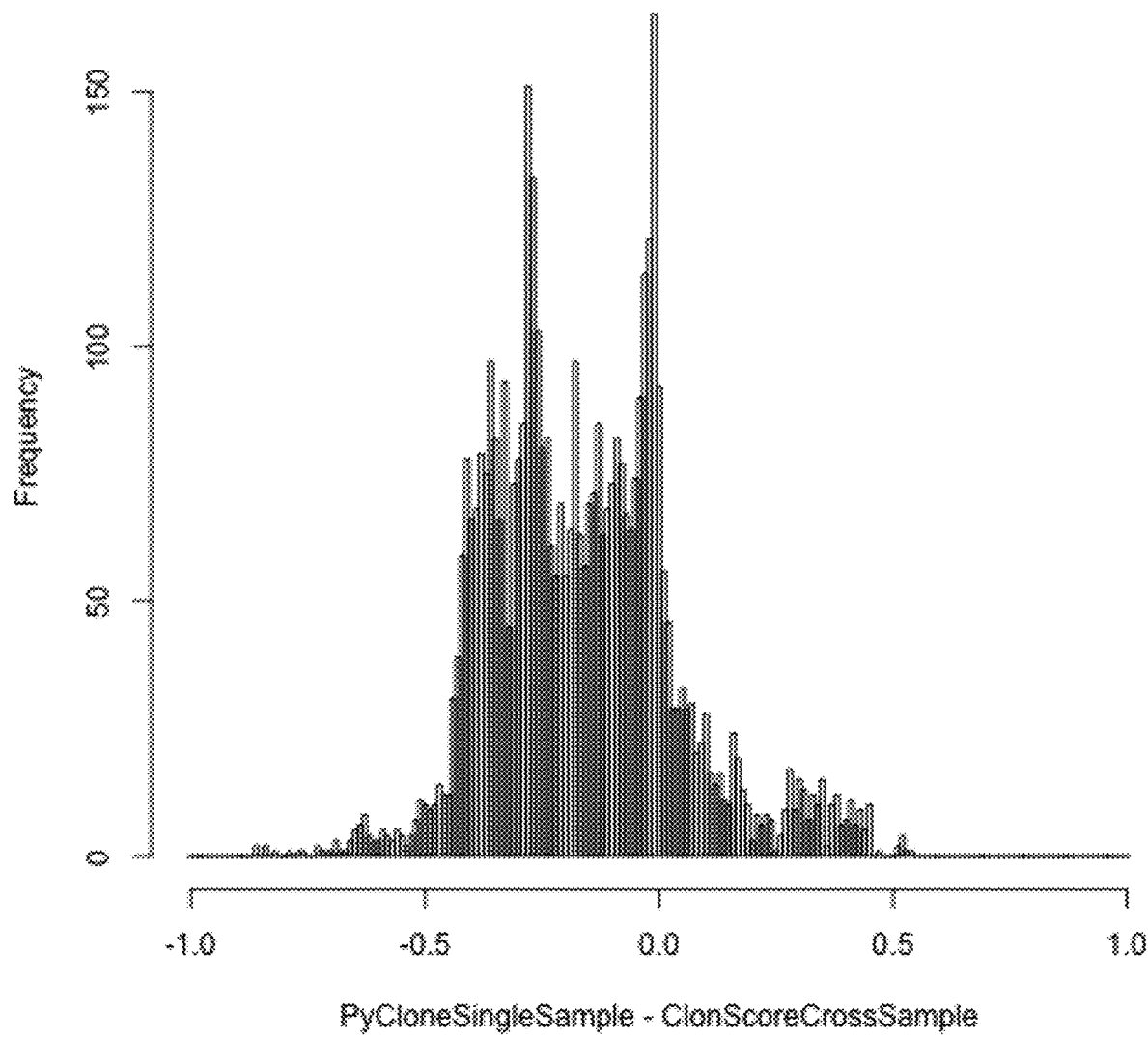

We then compared the CCF estimates made by ClonScore and PyClone in single tumor samples against the estimates made across multiple samples. We observed that ClonScore's estimates in single samples were highly consistent with the estimates made across samples by Hao (FIG. 20) PyClone (FIG. 21), and ClonScore (FIG. 22). PyClone's performance in single sample mode was surprisingly inconsistent with the estimates made across samples by Hao (FIG. 23), PyClone (FIG. 24), and ClonScore (FIG. 25).

Despite the encouraging consistency between ClonScore results in single samples and the CCF estimates across samples, the cross sample results are not necessarily true CCF values. Therefore, we evaluated ClonScore's performance by checking whether it was able to distinguish SNVs that are likely clonal from those that are likely subclonal. The way we defined the "true" clonal status of an SNV was by it being called in all four spatially separated tumor samples, and having cross sample CCF estimates (by cross sample ClonScore) greater than 90% in all four tumor samples. By determining that predicted clonal SNVs were those that single sample ClonScore assigned a CCF>95%, we observed 0.91 sensitivity and 0.89 specificity in clonal status prediction from single tumor samples. See Table 1 for results across the full dataset.

TABLE 1

True and predicated clonal and subcloneal SNVs

|  | True clonal | True subclonal |
|---|---|---|
| Predicted clonal | 1,252 | 3,755 |
| Predicted subclonal | 124 | 29,742 |

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method implemented using a computer system comprising one or more processors and system memory, the method comprising:
   (a) receiving, by the one or more processors, genomic sequence data obtained by sequencing nucleic acids in at least one test sample from a subject, wherein the nucleic acids are from one or more subclones of cancer cells;
   (b) determining a plurality of somatic mutation variants in the genomic sequence data;
   (c) calculating, for each somatic mutation variant and by the one or more processors, an initial cancer cell fraction (iCCF) using a VAF, wherein a cancer cell fraction is a fraction of cancer cells having the somatic mutation variant among all cancer cells, and wherein the VAF is an allele frequency of the somatic mutation variant, thereby obtaining a plurality of iCCFs for the plurality of somatic mutation variants;
   (d) clustering, by the one or more processors, the plurality of iCCFs for the plurality of somatic mutation variants, thereby obtaining one or more clusters of iCCFs, each cluster corresponding to variants present in a same subclone of the one or more subclones, wherein the clustering comprises determining one or more posterior probabilities of a mutation belonging to the one or more clusters;
   (e) determining, by the one or more processors, one or more final cancer cell fractions (fCCFs) for one or more somatic mutations of the plurality of somatic mutations using iCCFs of the one or more clusters, wherein the one or more fCCFs are determined using the one or more posterior probabilities and the plurality of iCCFs;
   (f) comparing the one or more fCCFs for the one or more somatic mutations to one or more criteria or threshold values associated with a clonality of the one or more somatic mutations within the one or more subclones of cancer cells and, based on the comparing, determining that the subject is likely to experience improvements from undergoing a therapy comprising a checkpoint inhibitor treatment regimen; and
   (g) treating the subject with the therapy comprising the checkpoint inhibitor treatment regimen.

2. The method of claim 1, further comprising:
   aligning sequence reads of the genomic sequence data to a reference genome to provide sequence tags, wherein the reference genome comprises a plurality of loci, each locus of the plurality of loci harboring a somatic mutation of a plurality of somatic mutations; and
   determining, for each locus of the plurality of loci, a coverage of the locus and a variant allele frequency (VAF) of the locus.

3. The method of claim 1, further comprising estimating a tumor purity value (p) that is a fraction of tumor cells among all cells in the test sample using the genomic sequence data.

4. The method of claim 1, further comprising estimating, for each locus of a plurality of loci, an average copy number of all alleles (N) at the locus for all cells in the test sample using the genomic sequence data.

5. The method of claim 4, wherein the initial cancer cell fraction (iCCF) is calculated using VAF, p, and N, wherein p is a fraction of tumor cells among all cells in the test sample using the genomic sequence data.

6. The method of claim 5, wherein the iCCF is calculated using a copy number of the variant allele of the somatic mutation (n), as well as VAF, p, and N.

7. The method of claim 6, wherein the iCCF is calculated based on (VAF*N)/(p*n).

8. The method of claim 7, wherein the iCCF is calculated with an assumption that n is 1.

9. The method of claim 8, wherein the iCCF is calculated based on: (i) (VAF*N)/p when (VAF*N)/p is not larger than 1, and (ii) 1 when (VAF*N)/p is larger than 1.

10. The method of claim 1, wherein an fCCF for a mutation is calculated as a linear combination of a mean iCCF of somatic mutations in each cluster and a posterior probability of the mutation belonging to each cluster.

11. The method of claim 10, wherein $fCCF_m$ for mutation m is calculated using the following formula:

$$fCCF_m = \sum_k (\overline{iCCF_k} \times pr_{m,k})$$

wherein
$\overline{iCCF_k}$ is the average iCCF of cluster k; and
$pr_{m,k}$ is the probability that mutation m belongs to cluster k.

12. The method of claim 11, wherein cluster k comprises a cluster of a highest probability for the mutation.

13. The method of claim 1, wherein the clustering comprises using a mixture model to determine the one or more clusters.

14. The method of claim 13, wherein the mixture model comprises a variational Bayesian mixture model.

15. The method of claim 13, wherein the clustering comprises determining a number of subclones giving rise to the one or more clusters of iCCFs.

16. The method of claim 15, wherein determining a subclone of the number of subclones comprises identifying a subset of the plurality of somatic sequence variants that cluster together based on estimated fractions of the subset all being within a predetermined range.

17. The method of claim 13, wherein the mixture model comprises a mixture of two or more probability distributions of variant allele counts for two or more clusters.

18. The method of claim 17, wherein each probability distribution of variant allele counts is selected from the group consisting of a binomial distribution, a beta distribution, a Gaussian distribution, and any combinations thereof.

19. The method of claim 18, wherein each probability distribution of variant allele counts is a binomial distribution.

20. The method of claim 18, wherein iCCF of a mutation is modeled as beta random variable having a beta distribution for a cluster.

21. The method of claim 20, wherein the at least one test sample comprises one sample, and a probability of a mutation belonging to a cluster is modeled as:

$$pr_{m,k} = \text{Beta}(f; u_k, v_k) = \frac{\Gamma(u_k + v_k)}{\Gamma(u_k)\Gamma(v_k)} f^{u_k - 1}(1 - f)^{v_k - 1}$$

wherein
$pr_{m,k}$ is a probability that mutation m belongs to cluster k;
Beta(;) is a probability density function of a beta distribution for cluster k;
f is iCCF for mutation m;
$\Gamma(\ )$ is a gamma function; and
$u_k$ and $v_k$ are shape parameters of the beta distribution for cluster k.

22. The method of claim 20, wherein the at least one test sample comprises two or more test samples, and a probability of a mutation belonging to a cluster is modeled as:

$$pr_{m,k} = p(f \mid u_k, v_k) = \text{Beta}(f; u_k, v_k) = \prod_{s=1}^{S} \text{Beta}(f; u_{ks}, v_{ks})$$

wherein $u_k$ and $v_k$ are shape parameter vectors whose $s^{th}$ components are $u_{ks}$ and $v_{ks}$, respectively.

23. The method of claim 1, wherein one or more mutations of the plurality of somatic mutations overlap with one or more copy number variations (CNVs).

24. The method of claim 1, wherein the method does not assume that all cancer cells are either affected by a CNV or not affected by the CNV.

25. The method of claim 24, wherein the method does not assume that all cancer cells carrying a somatic mutation are either affected by a CNV or not affected by the CNV.

26. The method of claim 1, wherein the clustering does not use Markov chain Monte Carlo (MCMC) methods.

27. The method of claim 1, wherein the plurality of somatic mutations comprises a mutation selected from the group consisting of a single nucleotide variant (SNV), an indel, or a combination thereof.

28. The method of claim 1, wherein the therapy comprises targeting a neoantigen associated with at least one of the one or more somatic mutations.

29. The method of claim 1, wherein the checkpoint inhibitor treatment regimen comprises anti-PD-1 therapy.

30. The method of claim 1, wherein the checkpoint inhibitor treatment regimen comprises administering pembrolizumab.

31. A method comprising:
  (a) receiving, by a computational system, genomic sequence data obtained by sequencing nucleic acids in at least one test sample from a subject, wherein the nucleic acids are from one or more subclones of cancer cells;
  (b) determining a plurality of somatic mutation variants in the genomic sequence data;
  (c) calculating, for each somatic mutation variant and by the computational system, an initial cancer cell fraction (iCCF) using a VAF, wherein a cancer cell fraction is a fraction of cancer cells having the somatic mutation variant among all cancer cells, and wherein the VAF is an allele frequency of the somatic mutation variant, thereby obtaining a plurality of iCCFs for the plurality of somatic mutation variants;
  (d) clustering, by the computational system, the plurality of iCCFs for the plurality of somatic mutation variants, thereby obtaining one or more clusters of iCCFs, each cluster corresponding to variants present in a same subclone of the one or more subclones, wherein the clustering comprises determining one or more posterior probabilities of a mutation belonging to the one or more clusters;
  (e) determining, by the computational system, one or more final cancer cell fractions (fCCFs) for one or more somatic mutations of the plurality of somatic mutations using iCCFs of the one or more clusters, wherein the one or more fCCFs are determined using the one or more posterior probabilities and the plurality of iCCFs;

(f) based on the one or more fCCFs, determining a clonality of the plurality of somatic mutation variants and wherein the clonality indicates that the subject is likely to experience improvements from undergoing a cancer therapy targeting one or more neoantigens associated with at least some of the plurality of somatic mutation variants; and (g) treating the subject with the cancer therapy comprising targeting the one or more neoantigens and a checkpoint inhibitor therapy.

32. The method of claim 31, wherein the checkpoint inhibitor therapy comprises anti-PD-1 therapy.

33. The method of claim 31, wherein the cancer therapy comprising targeting the one or more neoantigens is an immunotherapy.

34. The method of claim 31, wherein the checkpoint inhibitor therapy comprises administering pembrolizumab.

35. A method comprising:

(a) receiving, by a computational system, genomic sequence data obtained by sequencing nucleic acids in at least one test sample from a subject, wherein the nucleic acids are from one or more subclones of cancer cells;

(b) determining a plurality of somatic mutation variants in the genomic sequence data;

(c) calculating, for each somatic mutation variant and by the computational system, an initial cancer cell fraction (iCCF) using a VAF, wherein a cancer cell fraction is a fraction of cancer cells having the somatic mutation variant among all cancer cells, and wherein the VAF is an allele frequency of the somatic mutation variant, thereby obtaining a plurality of iCCFs for the plurality of somatic mutation variants;

(d) clustering, by the computational system, the plurality of iCCFs for the plurality of somatic mutation variants, thereby obtaining one or more clusters of iCCFs, each cluster corresponding to variants present in a same subclone of the one or more subclones, wherein the clustering comprises determining one or more posterior probabilities of a mutation belonging to the one or more clusters;

(e) determining, by the computational system, one or more final cancer cell fractions (fCCFs) for one or more somatic mutations of the plurality of somatic mutations using iCCFs of the one or more clusters, wherein the one or more fCCFs are determined using the one or more posterior probabilities and the plurality of iCCFs;

(f) based on the one or more fCCFs, determining a clonality of the plurality of somatic mutation variants and wherein the clonality indicates a neoantigen load of the one or more fCCFs, which neoantigen load indicates that the subject is likely to experience improvements from undergoing a cancer therapy comprising a checkpoint inhibitor therapy; and (g) treating the subject with the cancer therapy comprising an anti-PD-1 checkpoint inhibitor therapy.

36. The method of claim 35, wherein the cancer therapy further comprises an immunotherapy targeting one or more neoantigens associated with one or more of the plurality of somatic mutation variants.

37. The method of claim 35, wherein the anti-PD-1 checkpoint inhibitor therapy comprises administering pembrolizumab.

* * * * *